United States Patent
Khan et al.

(10) Patent No.: US 12,033,324 B2
(45) Date of Patent: Jul. 9, 2024

(54) SYSTEM AND METHOD FOR IDENTIFYING FRACTURES IN DIGITIZED X-RAYS

(71) Applicant: THE RESEARCH FOUNDATION FOR THE STATE UNIVERSITY OF NEW YORK, Albany, NY (US)

(72) Inventors: Fazel A. Khan, East Setauket, NY (US); Imin Kao, Stony Brook, NY (US); Carlos Gabriel Helguero, Guayaquil (EC)

(73) Assignee: The Research Foundation for The State University of New York, Albany, NY (US)

(*) Notice: Subject to any disclaimer, the term of this patent is extended or adjusted under 35 U.S.C. 154(b) by 386 days.

(21) Appl. No.: 17/619,085

(22) PCT Filed: Jun. 8, 2020

(86) PCT No.: PCT/US2020/036564
§ 371 (c)(1),
(2) Date: Dec. 14, 2021

(87) PCT Pub. No.: WO2020/247902
PCT Pub. Date: Dec. 10, 2020

(65) Prior Publication Data
US 2022/0301281 A1    Sep. 22, 2022

Related U.S. Application Data

(60) Provisional application No. 62/857,865, filed on Jun. 6, 2019.

(51) Int. Cl.
*G06T 7/00*      (2017.01)
*A61B 6/00*      (2006.01)
(Continued)

(52) U.S. Cl.
CPC ............ *G06T 7/0012* (2013.01); *A61B 6/505* (2013.01); *A61B 6/5205* (2013.01); *G06T 5/40* (2013.01);
(Continued)

(58) Field of Classification Search
CPC .......... G06T 7/0012; G06T 5/40; G06T 5/92; G06T 7/11; G06T 7/12; G06T 11/00;
(Continued)

(56) References Cited

U.S. PATENT DOCUMENTS 4,367,490 A    1/1983   Riederer
4,458,267 A    7/1984   Dolazza
(Continued)

FOREIGN PATENT DOCUMENTS

CN    111867451 A    10/2020
DE    10334119 A1    5/2004
(Continued)

OTHER PUBLICATIONS

Hrzic et al., "Local-Entropy Based Approach for X-Ray Image Segmentation and Fracture Detection"; retrieved from the Internet: URL: https://www.mdpi.com/1099-4300/21/4/338/pdf; pp. 1-18; Mar. 2019.
(Continued)

*Primary Examiner* — Tom Y Lu
(74) *Attorney, Agent, or Firm* — Hoffmann & Baron, LLP

(57) ABSTRACT

A method for identifying one or more fractures in a digitized x-ray image includes: obtaining a digitized x-ray image; performing preprocessing on the digitized x-ray image to generate a modified x-ray image having enhanced resolution; partitioning the modified x-ray image into a two-dimensional array including multiple pixels; obtaining an intensity of each of the pixels in the modified x-ray image; evaluating each of the pixels in the modified x-ray image to
(Continued)

determine whether at least a given one of the pixels has an intensity indicative of a black pixel; for each given pixel having an intensity indicative of a black pixel, flagging the given pixel when pixels immediately adjacent to the given pixel have an intensity greater than a prescribed threshold value; and placing a visual indication of a possible fracture on the modified x-ray image corresponding to a location of each flagged pixel.

20 Claims, 18 Drawing Sheets

(51) Int. Cl.
| | |
|---|---|
| *A61B 6/50* | (2024.01) |
| *G06T 5/40* | (2006.01) |
| *G06T 5/92* | (2024.01) |
| *G06T 7/11* | (2017.01) |
| *G06T 7/12* | (2017.01) |
| *G06T 11/00* | (2006.01) |
| *G06V 10/28* | (2022.01) |
| *G06V 10/75* | (2022.01) |
| *G06V 10/776* | (2022.01) |
| *G16H 30/40* | (2018.01) |

(52) U.S. Cl.
CPC ............... *G06T 5/92* (2024.01); *G06T 7/11* (2017.01); *G06T 7/12* (2017.01); *G06T 11/00* (2013.01); *G06V 10/28* (2022.01); *G06V 10/751* (2022.01); *G06V 10/776* (2022.01); *G16H 30/40* (2018.01); *G06T 2207/10116* (2013.01); *G06T 2207/30008* (2013.01); *G06V 2201/033* (2022.01)

(58) Field of Classification Search
CPC . G06T 2207/10116; G06T 2207/30008; A61B 6/505; A61B 6/5205; A61B 6/5217; G06V 10/28; G06V 10/751; G06V 10/776; G06V 2201/033; G16H 30/40
See application file for complete search history.

(56) References Cited

U.S. PATENT DOCUMENTS

| | | | |
|---|---|---|---|
| 4,573,035 A | 2/1986 | Dolazza | |
| 4,618,990 A | 10/1986 | Sieb, Jr. et al. | |
| 4,636,850 A | 1/1987 | Stewart | |
| 4,644,575 A | 2/1987 | Kruger et al. | |
| 4,736,399 A | 4/1988 | Okazaki | |
| 4,792,900 A | 12/1988 | Sones et al. | |
| 5,150,394 A | 9/1992 | Karellas | |
| 5,194,746 A | 3/1993 | Gunther et al. | |
| 5,297,551 A | 3/1994 | Margosian et al. | |
| 5,598,185 A | 1/1997 | Holmgren | |
| 5,617,313 A | 4/1997 | Namiki | |
| 5,740,267 A | 4/1998 | Echerer et al. | |
| 5,896,463 A | 4/1999 | Kuhn | |
| 5,978,443 A | 11/1999 | Patel | |
| 6,167,113 A | 12/2000 | Armentrout et al. | |
| 6,370,224 B1 | 4/2002 | Simon et al. | |
| 6,529,622 B1 | 3/2003 | Pourjavid | |
| 6,606,171 B1 | 8/2003 | Renk et al. | |
| 6,731,798 B1 | 5/2004 | Stearns | |
| 6,747,697 B1 | 6/2004 | Lin et al. | |
| 6,768,784 B1 | 7/2004 | Green et al. | |
| 6,990,239 B1 | 1/2006 | Nelson | |
| 7,023,576 B1 | 4/2006 | Michael et al. | |
| 7,054,474 B1 | 5/2006 | Krieger | |
| 7,263,214 B2 * | 8/2007 | Uppaluri | G16H 30/20 382/128 |
| 8,064,660 B2 * | 11/2011 | Leow | G03B 42/02 382/128 |
| 9,080,439 B2 * | 7/2015 | O'Malley | E21B 33/13 |
| 10,089,956 B2 | 10/2018 | Awad et al. | |
| 10,376,230 B2 * | 8/2019 | Wehnes | G16H 50/30 |
| 2002/0080917 A1 | 6/2002 | Granfors et al. | |
| 2004/0017629 A1 | 1/2004 | Lamberts et al. | |
| 2004/0200969 A1 | 10/2004 | Odogba et al. | |
| 2005/0213849 A1 | 9/2005 | Kreang-Arekul et al. | |
| 2007/0274584 A1 | 11/2007 | Leow et al. | |
| 2008/0217545 A1 | 9/2008 | Liu et al. | |
| 2011/0013817 A1 | 1/2011 | Medow | |
| 2013/0079626 A1 | 3/2013 | Shmatukha | |
| 2013/0343622 A1 | 12/2013 | Ruiz et al. | |
| 2014/0233820 A1 * | 8/2014 | Wu | A61B 6/5211 382/131 |
| 2016/0296188 A1 | 10/2016 | Zebaze et al. | |
| 2017/0374295 A1 | 12/2017 | Topfer et al. | |
| 2018/0101937 A1 | 4/2018 | Borsholm et al. | |
| 2018/0268544 A1 | 9/2018 | Westerhoff et al. | |

FOREIGN PATENT DOCUMENTS

| | | |
|---|---|---|
| EP | 0066824 A2 | 12/1982 |
| EP | 0314506 A1 | 5/1989 |
| EP | 0383269 A2 | 8/1990 |
| EP | 0609922 B1 | 8/1994 |
| EP | 0779770 A1 | 6/1997 |
| EP | 0954940 A2 | 11/1999 |
| EP | 1795918 A2 | 6/2007 |
| EP | 2192422 A1 | 6/2010 |
| JP | H0666911 B2 | 8/1994 |
| JP | H06251127 A | 9/1994 |
| JP | H0756674 B2 | 6/1995 |
| JP | H08272951 A | 10/1996 |
| JP | H08294480 A | 11/1996 |
| JP | H10924040 A | 1/1997 |
| JP | H09138849 A | 5/1997 |
| JP | H10137229 A | 5/1998 |
| JP | H11505142 A | 5/1999 |
| JP | 2000182062 A | 6/2000 |
| JP | 2001155143 A | 6/2001 |
| JP | 3290483 B2 | 6/2002 |
| JP | 2002232784 A | 8/2002 |
| JP | 2003175022 A | 6/2003 |
| JP | 4063324 B2 | 3/2008 |
| JP | 2008524874 A | 7/2008 |
| JP | 2011104055 A | 6/2011 |
| JP | 4782902 B2 | 9/2011 |
| JP | 2013098995 A | 5/2013 |
| JP | 5404179 B2 | 1/2014 |
| WO | 9417493 A1 | 8/1994 |
| WO | 1996002897 A2 | 2/1996 |
| WO | 2000077503 A1 | 12/2000 |
| WO | 2015017210 A1 | 2/2015 |
| WO | 2020247902 A1 | 12/2020 |

OTHER PUBLICATIONS

Porter et al., "Automated Measurement of Fracture Callus in Radiographs Using Portable Software," Journal of Orthopaedic Research; retrieved from the Internet: URL: https://www.ncbi.nlm.nih.gov/pmc/articles/PMC5166988/pdf/nihms835583.pdf; pp. 1-20; Dec. 2016.

Krug et al., "High-resolution Imaging Techniques for the Assessment of Osteoporosis," Radiologic Clinics North America; retrieved from Internet: URL: https://www.ncbi.nlm.nih.gov/pmc/articles/PMC2901255/pdf/nihms182082.pdf; pp. 1-36; May 2011.

Cephas et al., "A Robust Approach for Detection of the type of Fracture from X-Ray Images," International Journal of Advanced Research in Computer and Communication Engineering, vol. 4, Issue 3; retrieved from Internet: URL: https://www.ijarcce.com/upload/2015/march15/IJARCCE%20114.pdf; pp. 479-482; Mar. 2015.

\* cited by examiner

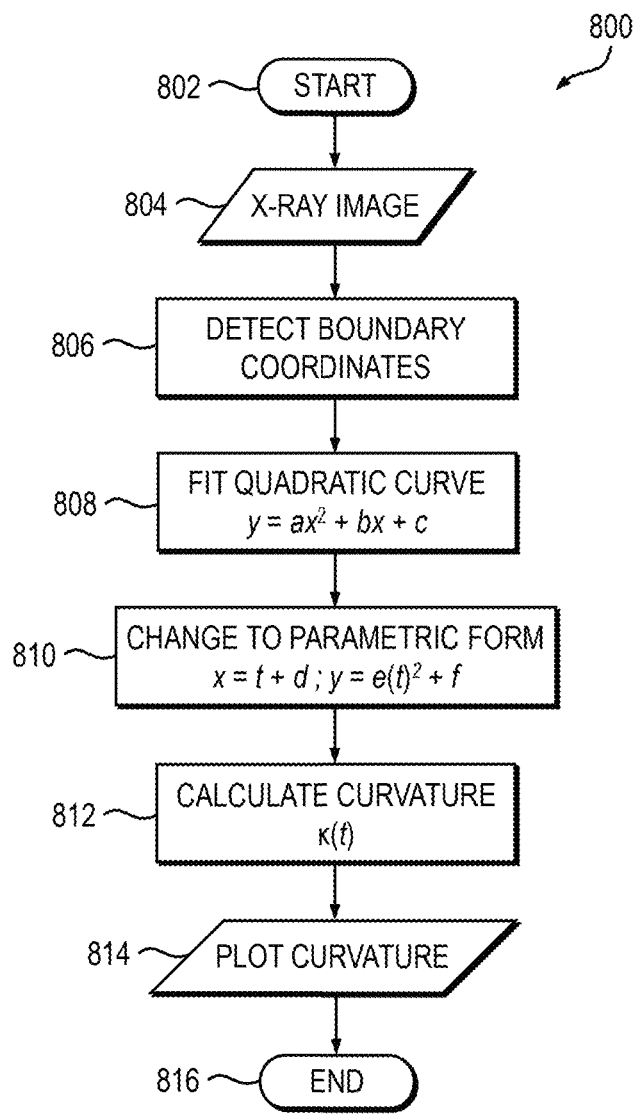

*FIG. 9A*            *FIG. 9B*
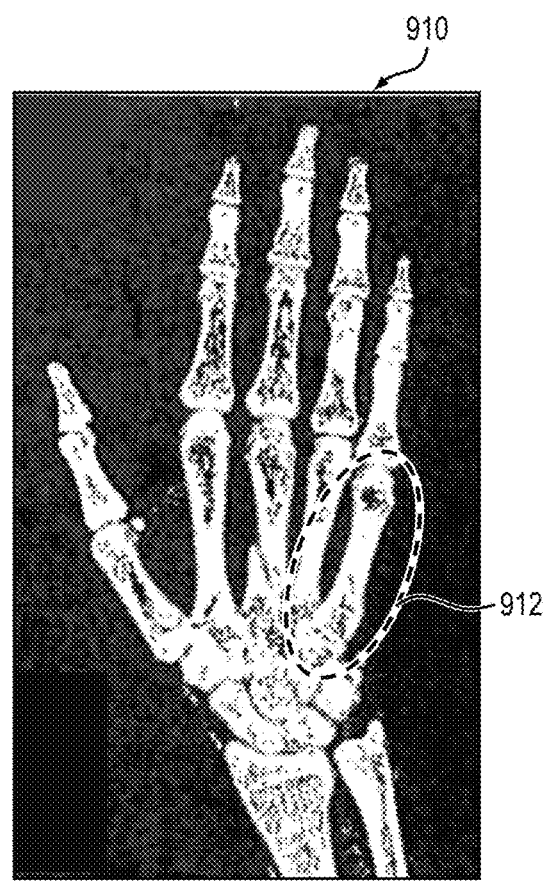

SYSTEM AND METHOD FOR IDENTIFYING FRACTURES IN DIGITIZED X-RAYS

CROSS-REFERENCE TO RELATED APPLICATIONS

This application is the U.S. national phase application of international application no. PCT/US2020/036564 filed on 8 Jun. 2020, which claims priority to provisional application No. 62/857,865 filed on 6 Jun. 2019, entitled "System and Method to Identify Fractures in Digitized X-Rays," the disclosures of which are incorporated by reference herein in their entirety for all purposes.

BACKGROUND

The present invention relates generally to the electrical, electronic and computer arts, and, more particularly, relates to the identification of fractures in digitized x-rays.

Musculoskeletal injuries are one of the most common reasons for patients to visit a medical office, be it in a primary physician's office, an orthopedic surgeon's office, an emergency room, or an urgent care (i.e., "stat health") facility. X-rays are routinely performed in this setting and are almost universally accepted as the standard for diagnosing an orthopedic condition.

A patient may be noted to have an obvious fracture that requires urgent treatment, with clear "displacement" of the fracture fragment. In this scenario, it is very easy for an attending physician to read the x-ray to identify the problem. In some instances, however, the fracture is minimally displaced (often referred to colloquially as a "hairline crack"). In these instances, the physician reading the x-ray, or even a radiologist, might sometimes miss this finding on the x-ray; there is a surprisingly high incidence of such fractures that are missed while reading the x-ray.

The effect of a missed fracture can have devastating medical and legal consequences. For example, if a patient with an undiagnosed hairline fracture is discharged from a medical care facility without appropriate treatment (which may consist of anything from modified weight bearing with the use of crutches/cane, cast application, and/or even surgery), the fracture has a real risk of displacing and progressing to a nonunion (i.e., non-healing) state. Even if the fracture is eventually recognized at a later date, the treatment approach could become significantly more complex or risky, sometimes transforming what should have initially been a non-operative treatment into an operative one.

SUMMARY

The present invention, as manifested in one or more embodiments thereof, is directed to methods and apparatus for reading a digitized x-ray and generating an output for identifying whether or not there is a fracture present on the x-ray. In one or more embodiments, novel software is provided which treats the x-ray as a collection of pixels. Since x-rays are essentially grayscale images, a given x-ray can be represented using a two-dimensional matrix array of numbers, with each matrix element containing one of a range of numbers (e.g., from 0 to 255), representing the shade of gray that each pixel contains, according to aspects of the invention. Once each pixel in the digitized x-ray image is assigned a number representing its shade of gray, embodiments of the invention perform an image processing methodology for analyzing the digitized x-ray image for hairline cracks and other fractures.

High sensitivity of the image processing application may generate false indications of a fracture. Therefore, in order to reduce these false indications and improve the confidence and accuracy of the output result, one or more embodiments of the invention optionally utilize machine learning techniques to identify bone segments having a high likelihood of fracture and extract such bone segments for further processing using an image processing algorithm to extract the location of a hairline crack.

In accordance with an embodiment of the invention, a method for identifying one or more fractures in a digitized x-ray image includes: obtaining a digitized x-ray image; performing preprocessing on the digitized x-ray image to generate a modified x-ray image having enhanced resolution; partitioning the modified x-ray image into a two-dimensional array comprising a plurality of pixels; obtaining an intensity of each of the plurality of pixels in the modified x-ray image; evaluating each of the plurality of pixels in the modified x-ray image to determine whether at least a given one of the plurality of pixels has an intensity indicative of a black pixel; for each given pixel having an intensity indicative of a black pixel, flagging the given pixel when pixels immediately adjacent to the given pixel have an intensity greater than a prescribed threshold value; and placing a visual indication of a possible fracture on the modified x-ray image corresponding to a location of each flagged pixel.

In accordance with another embodiment of the invention, an apparatus for identifying fractures in a digitized x-ray image includes memory and one or more processors coupled with the memory. The processor(s) is configured: to obtain a digitized x-ray image; to perform preprocessing on the digitized x-ray image to generate a modified x-ray image having enhanced resolution; to partition the modified x-ray image into a two-dimensional array comprising a plurality of pixels; to obtain an intensity of each of the plurality of pixels in the modified x-ray image; to evaluate each of the plurality of pixels in the modified x-ray image to determine whether at least a given one of the plurality of pixels has an intensity indicative of a black pixel; for each given pixel having an intensity indicative of a black pixel, to flag the given pixel when pixels immediately adjacent to and within a prescribed range of the given pixel have an intensity greater than a prescribed threshold value; and to place a visual indication of a possible fracture on the modified x-ray image corresponding to a location of each flagged pixel.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a non-transitory computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques as disclosed herein can provide substantial beneficial technical effects. By way of example only and without limitation, one or more embodiments of the invention may provide one or more of the following advantages:
improved diagnosis and treatment for a patient;
reduces the likelihood of a physician missing a fracture in reading an x-ray;
allows interns, residents and physician assistants working in real time (e.g., overnight call setting) to reduce the likelihood of making mistakes in reading an x-ray without review by an attending physician;
utilizes fracture detection techniques, including, but not limited to, image processing, boundary detection, curvature analysis and/or machine learning, to identify bone segments having a high likelihood of fracture, to thereby reduce false indications and improve confidence and accuracy in the output result.

These and other features and advantages will become apparent from the following detailed description of illustrative embodiments thereof, which is to be read in connection with the accompanying drawings.

BRIEF DESCRIPTION OF THE DRAWINGS

Non-limiting and non-exhaustive embodiments of the present invention will be described with reference to the following drawings which are presented by way of example only, wherein like reference numerals (when used) indicate corresponding elements throughout the several views unless otherwise specified, and wherein:

FIG. 8 is a flow diagram depicting at least a portion of an exemplary method for determining the curvature of a boundary of interest to enhance the accuracy of fracture detection in a digitized x-ray, according to an embodiment of the invention;

FIGS. 9A and 9B are an exemplary grayscale x-ray image and a corresponding black and white x-ray image after performing image preprocessing, respectively, without any fractures;

Figure 1:
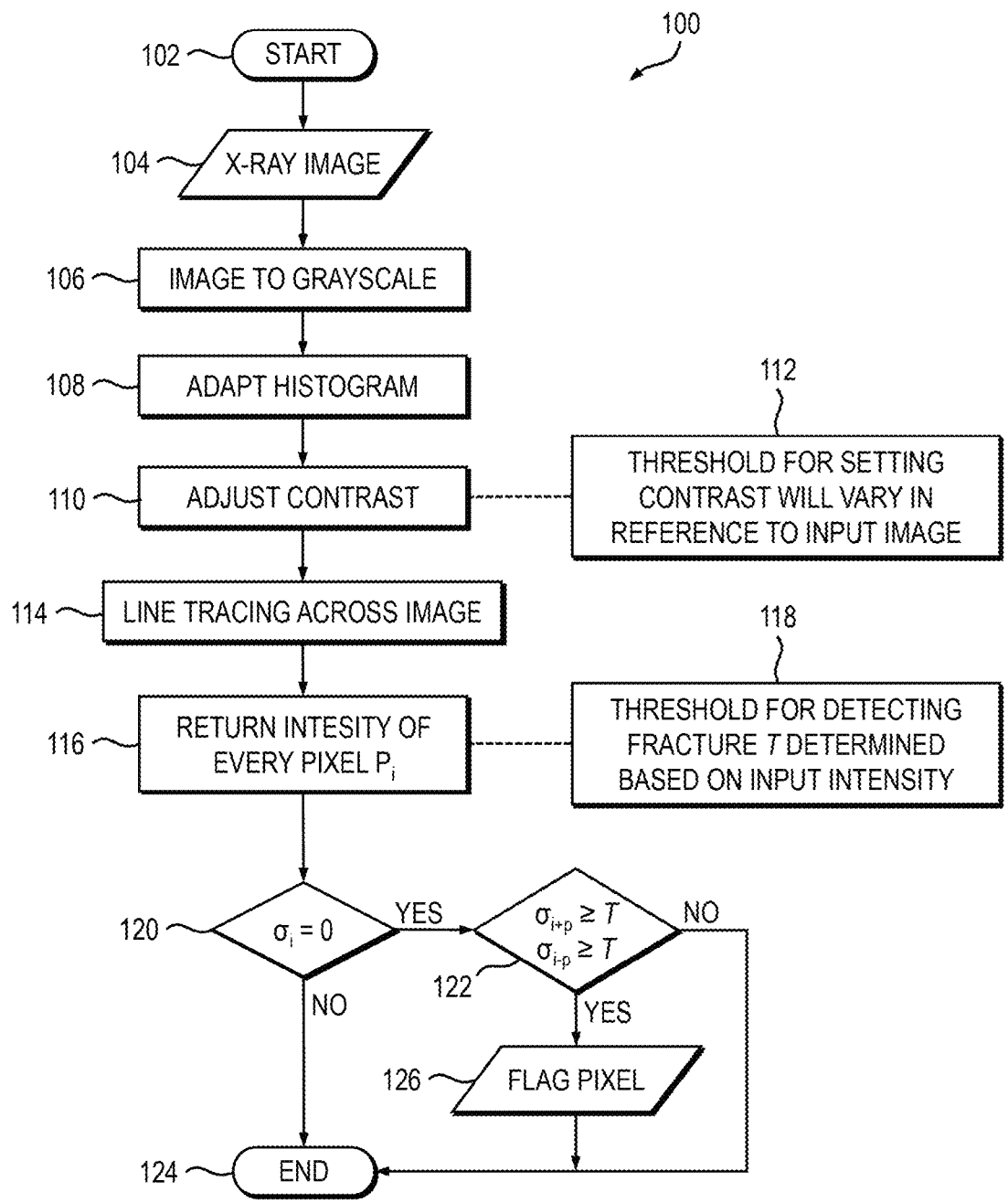
FIG. 1 is a top-level flow diagram depicting at least a portion of an exemplary method for assigning pixel intensity in a digitized x-ray image as part of an overall fracture detection process, according to an embodiment of the present invention.

It is to be appreciated that elements in the figures are illustrated for simplicity and clarity. Common but well-understood elements that may be useful or necessary in a commercially feasible embodiment may not be shown in order to facilitate a less hindered view of the illustrated embodiments.

DETAILED DESCRIPTION

Principles of the present disclosure will be described herein in the context of illustrative methods and apparatus for identifying fractures in a digitized x-ray. It is to be appreciated, however, that the specific methods and/or apparatus illustratively shown and described herein are to be considered exemplary as opposed to limiting. Moreover, it will become apparent to those skilled in the art given the teachings herein that numerous modifications can be made to the embodiments shown that are within the scope of the appended claims. That is, no limitations with respect to the embodiments shown and described herein are intended or should be inferred.

In some instances, when a patient has a fracture that is minimally displaced (i.e., a "hairline crack"), there is a high incidence that such fracture will be missed by a physician or radiologist reading the x-ray. In order to reduce the likelihood of such a missed fracture diagnosis, embodiments of the present invention provide methods and apparatus for reading a digitized x-ray and generating an output, preferably superimposed directly on the x-ray image, identifying whether or not there is a possible fracture present. In one or more embodiments, novel software is provided which essentially partitions the x-ray into a plurality of pixels. Since x-rays are typically grayscale images, a given x-ray is represented using a two-dimensional matrix array of numbers, with each matrix element containing one of a range of numbers (e.g., from 0 (black) to 255 (white)) representing a shade of white associated with each pixel, according to aspects of the invention. Once each pixel in the digitized x-ray image is assigned a number representing its shade of white, embodiments of the invention perform an image processing methodology for analyzing the digitized x-ray image for hairline cracks and other fractures.

As an overview, a method according to one or more embodiments of the invention evaluates each pixel in the digitized x-ray image using a local geometry analysis and searches for a sudden point in the image where there is darkness surrounded by bright whiteness, representing a fracture line surrounded by two ends of bone that have broken or otherwise separated. This occurrence corresponds to a mathematical "gradient" when represented numerically. In some embodiments, the method employs an edge detection algorithm to outline a perimeter of each bone. The resulting curves are best-fitted into a mathematical formula (e.g., y=f(x)). When there is a fracture present, there will be a sudden change in the parameters of the curve compared to normal bone. Optionally, advanced image processing of the original digitized x-ray image is performed to optimize the image resolution so as to preprocess the image before applying edge detection or local geometry analysis.

In one or more embodiments of the invention, an output is presented, preferably by generating circles or other visual indications (e.g., highlighting, boxes, etc.) at any point on the x-ray image where there is a reasonable likelihood of a fracture. In this manner, the physician or radiologist will be alerted to carefully review a particular region or regions to discover a hairline crack that otherwise may have been missed. The physician makes the final determination of whether or not the alerted region(s) represents a real fracture or a false positive based on personal review of the image and clinical scenario (e.g., whether the patient is complaining of tenderness in that region).

With reference now to the drawings, FIG. 1 is a top-level flow diagram depicting at least a portion of an exemplary method 100 for assigning pixel intensity in a digitized x-ray image as part of an overall fracture detection process, according to an embodiment of the invention. The method 100 begins in step 102, which may include an initialization procedure for setting certain registers, arrays, variables, etc., to known values (e.g., zero) for subsequent use in the method. In step 104, the method 100 receives, as an input, a digitized x-ray image to be analyzed for the presence of fractures. Prior to conducting a pixel-wise scan of the x-ray image, one or more image processing routines are optionally performed to enhance the image resolution or otherwise optimize the image to improve an accuracy of the fracture identification.

Figure 2:
FIG. 2 conceptually depicts an exemplary grayscale image after conversion from an original input RGB x-ray image in an image preprocessing step of the exemplary method shown in FIG. 1, according to an embodiment of the present invention.

Since the digitized input x-ray image is often generated as an RGB (red, green and blue) image, step 106 converts the image to a grayscale image. FIG. 2 conceptually depicts an exemplary grayscale image 200 after conversion from the original input RGB x-ray image in step 106, according to an embodiment of the invention. As apparent from the grayscale image 200, a region 202 indicates a hairline fracture that is essentially indiscernible, and is therefore likely to be missed by an attending physician or radiologist.

With continued reference to FIG. 1, a histogram of the grayscale image is then adapted in step 108, such as by performing histogram equalization. In an image processing context, the histogram of an image normally refers to a histogram of the pixel intensity values. This histogram is a graph showing the number of pixels in an image at each different intensity value found in that image. For example, for an 8-bit grayscale image there are 256 different possible intensities, and so the histogram will graphically display 256 numbers showing the distribution of pixels amongst those grayscale values. Histogram equalization, also referred to as histogram normalization, usually increases the global contrast of many images, especially when the usable data of the image is represented by close contrast values. Through this adjustment, the intensities can be better distributed on the histogram, which allows for areas of lower local contrast to gain a higher contrast. Histogram equalization accomplishes this by effectively spreading out the most frequent intensity values. Thus, in one or more embodiments, adapting the histogram of the grayscale image in step 108 preferably involves equalizing pixel intensities throughout the image.

Figure 3A:
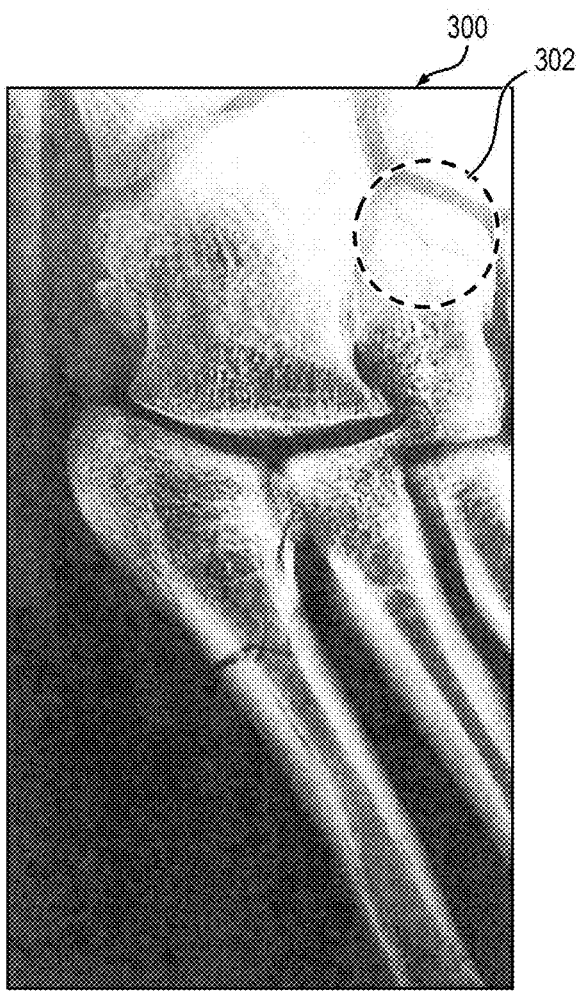
FIG. 3A conceptually depicts an exemplary grayscale image after adapting a histogram of the grayscale x-ray image in an image preprocessing step of the illustrative method shown in FIG. 1, according to an embodiment of the present invention.

FIG. 3A conceptually depicts an exemplary grayscale image 300 after adapting a histogram of the grayscale x-ray image in step 108, according to an embodiment of the invention. As apparent from the image 300, an intensity, particularly of the white areas, of the image has been normalized. In a region 302 of the image 300, which corresponds to the region 202 shown in FIG. 2, the hairline fracture is beginning to become more visible compared to the grayscale image 200 of FIG. 2.

Returning now to FIG. 1, in a further image preprocessing step 110, a contrast of the output image generated in step 108 is adjusted to a prescribed optimal range. Thresholds 112 for setting the image contrast are preferably supplied as input parameters for step 110 and will vary in reference to the particular input image. Although the present invention contemplates various ways to perform image contrast adjustment, one way to achieve this is by using a MATLAB® (a registered trademark of The Math Works, Inc. of Natick, MA) image processing toolbox command, imadjust( ). One syntax for the imadjust( ) command is as follows:

$$J=\text{imadjust}(I,[\text{low\_in high\_in}],[\text{low\_out high\_out}], \text{gamma}),$$

which maps intensity values in a grayscale image I to new values in J such that intensity values between low_in and high_in map to values between low_out and high_out, and where gamma specifies the shape of a curve describing the relationship between the values in I and J.

Figure 3B:
FIG. 3B conceptually depicts an exemplary grayscale image after adjusting a contrast of the grayscale x-ray image in an image preprocessing step of the illustrative method shown in FIG. 1, according to an embodiment of the present invention.

FIG. 3B conceptually depicts an exemplary grayscale image 310 after adjusting a contrast of the grayscale x-ray image in step 110, according to an embodiment of the invention. As apparent from the image 310, a contrast of the image has been adjusted. In a region 312 of the image 310, which corresponds to the regions 202 and 302 shown in FIGS. 2 and 3A, respectively, the hairline fracture is now clearly visible compared to the image 300 of FIG. 3A. The image preprocessing steps 106, 108 and 110 produce a modified x-ray image (image 310 shown in FIG. 3B) which is superior, compared to the original grayscale image 200 shown in FIG. 2, and will beneficially provide enhanced accuracy of subsequent pixel evaluation steps performed by the method 100.

Figure 4A:
FIG. 4A conceptually depicts an exemplary grayscale image generated as an output of an image preprocessing step of the illustrative method shown in FIG. 1, arranged as a two-dimensional matrix of pixels, according to an embodiment of the present invention.

More particularly, referring to FIG. 1, after performing optional image preprocessing (e.g., steps 106, 108, 110), the exemplary method 100 preferably searches the image for indications of a possible fracture or crack. To accomplish this, the method 100 performs a line tracing routine across the x-ray image in step 114. This line tracing routine may involve partitioning the image into a two-dimensional matrix array, organized as a plurality of horizontal and vertical lines, with a pixel disposed at each intersection of a unique horizontal and vertical line. FIG. 4A conceptually depicts an image 400, generated as an output of step 110, partitioned into a two-dimensional matrix of pixels, according to an embodiment of the invention. Step 114 traces the lines horizontally and vertically throughout the image. Generally, the smaller the pixel size, the higher the resolution, although it is to be understood that embodiments of the invention are not limited to any specific pixel size.

In step 116, an intensity value ($\sigma_i$) of each pixel, $P_i$, in the image is obtained. In one or more embodiments, these pixel intensity values $\sigma_i$ are preferably stored in a two-dimensional array, or other storage element, specifically correlating to the x-ray image. The presence of a fracture may be determined when a pixel having a black (e.g., 0) intensity value is accompanied by directly adjacent pixels (e.g., on either side along a horizontal or vertical line) having a white intensity value; in an x-ray image, a fracture is generally indicated as a black line surrounded by white areas indicative of bone.

At least one threshold (T) 118 for detecting the presence of a fracture is preferably provided as an input parameter to step 116. Optionally, in some embodiments, multiple thresholds can be used corresponding to different sensitivity levels of the line tracing routine. Thus, a threshold that is set mid-way between black and white intensities is more likely to produce false positives, but a threshold value that is set close to the black intensity may not detect the presence of a fracture in some cases. By way of example only and without limitation, in an 8-bit grayscale image, assuming an intensity value of zero is indicative of a purely black pixel and an intensity value of 255 is indicative of a purely white pixel, a threshold may be set to a value of 64 to detect a black pixel surrounded by pixels having an intensity of at least 25% white.

In step 120, the method 100 checks each pixel $P_i$ in the image to determine whether it has an intensity value $\sigma_i$ equal to zero, indicative of a black pixel (i.e., $\sigma_i=0$). If a current pixel being scanned is found to have an intensity value equal to zero (i.e., a black pixel), the method, in step 122, checks the intensity of each of a prescribed number of pixels, p, adjacent to and in the vicinity of the detected black pixel along a scanned line (i.e., neighboring pixels in a given scan line); the intensity, $\sigma_{i-p}$, of an immediately preceding pixel along the scanned line, and the intensity, $\sigma_{i+p}$, of an immediately succeeding pixel along the scanned line is checked to see if it exceeds a prescribed threshold, T. More particularly, in one or more embodiments, when a current pixel $P_i$ is detected having an intensity equal to zero (black), step 122 checks the intensity of immediately adjacent pixels, $P_{i+1}$ and $P_{i-1}$, as well as pixels in a prescribed range (i.e., vicinity) of the immediately adjacent pixels, $P_{i+p}$ and $P_{i-p}$, where p is an integer controlling the number (i.e., depth) of pixels being checked in the vicinity of the detected black pixel. In an exemplary embodiment, a pixel depth of p=5 was found to be a good measure, since hairline fractures are typically about 2 to 3 pixels thick, depending on the size of the pixels used. Furthermore, assuming the x-ray image is partitioned into a standard x-y grid, in one or more embodiments, pixels at a depth of p from the detected black pixel are checked in all four directions (top, bottom, left, right).

Alternatively, if the intensity $\sigma_i$ of the current pixel being scanned in step 120 is found to have an intensity that is not equal to zero (i.e., a non-black pixel), the method 100 continues to advance to the next pixel in the scanned line until all pixels in the image have been evaluated, at which point the method ends at step 124.

When, in step 122, it is determined that each of the pixels immediately surrounding or in the prescribed vicinity of a detected black have an intensity that equals or exceeds the prescribed threshold T for detecting a fracture, the detected black pixel is flagged in step 126, and the process repeats until all pixels in the image have been evaluated, after which the method ends at step 124. Alternatively, when one or both pixels surrounding the detected black pixel are determined in step 122 to have an intensity that does not exceed the prescribed threshold T, that detected black pixel is not flagged and the method continues to evaluate the remaining pixels in the image, eventually ending at step 124.

Figure 4B:
FIG. 4B conceptually depicts an exemplary grayscale image including flagged pixels generated as an output after completion of the illustrative method shown in FIG. 1, according to an embodiment of the present invention.

The process of flagging pixels indicative of a possible fracture (i.e., pixels of interest) in the x-ray image in step 126 may, in one or more embodiments, comprise adding a visual indication on the x-ray image, such as placing a circle, or other shaped object, at the location of each flagged pixel. For example, FIG. 4B conceptually depicts an exemplary grayscale image 410 including flagged pixels generated as an output of step 126, after completion of the illustrative method 100 shown in FIG. 1, according to an embodiment of the invention. As apparent from FIG. 4B, circles are placed on the image 410 in a region 412 showing the location of each pixel of interest. Collectively, these flagged pixels in region 412 beneficially indicate a possible detected fracture in the image.

Figure 5:
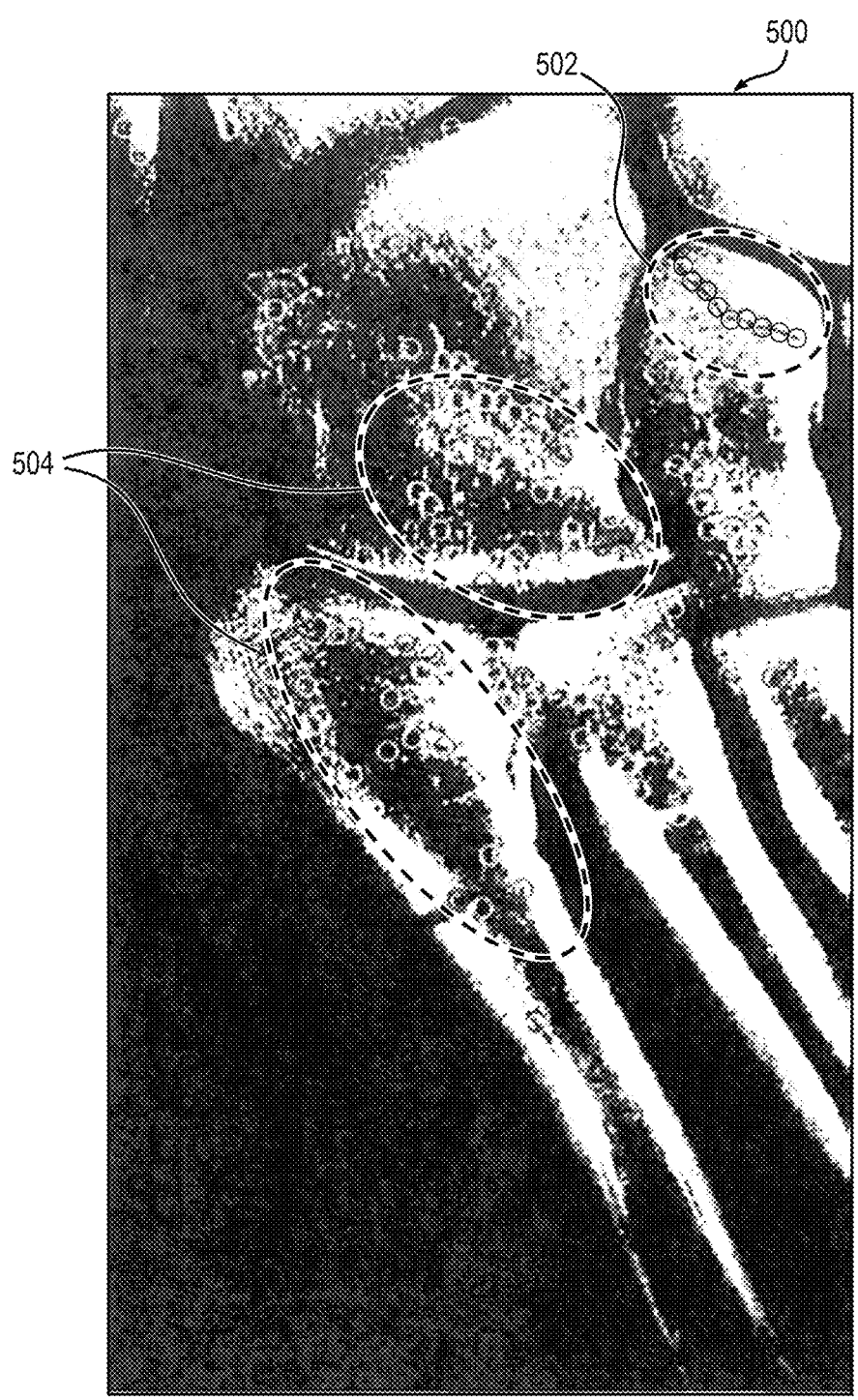
FIG. 5 conceptually depicts an exemplary grayscale image including pixels that were flagged as containing a fracture by the method shown in FIG. 1, according to an embodiment of the present invention.

Ideally, the method in accordance with embodiments of the invention should only detect and flag pixels indicative of an actual fracture. However, due to distortions and other impurities in the x-ray image, the method has a much higher sensitivity and will therefore likely produce false indications of fractures (i.e., false positives). For example, FIG. 5 conceptually depicts an exemplary image 500 including pixels that were flagged as containing a fracture by the illustrative method 100 shown in FIG. 1, according to an embodiment of the invention. As apparent from FIG. 5, the image 500 includes a region 502 containing flagged pixels correctly indicating a fracture, but it also includes regions 504 containing flagged pixels resulting from inconsistencies, distortions or other imperfections in the input x-ray image, falsely indicating the presence of a bone fracture.

In order to reduce the number of false indications generated by the illustrative method 100, embodiments of the invention advantageously employ one or more routines that improve an accuracy of the output indication generated by the method 100. Such routines, including curvature deviation with edge detection, boundary scanning, spline fitting and machine learning, among others, when used in conjunction with the illustrative method 100, provide a more accurate prediction regarding the presence of a true fracture in a digitized x-ray image.

Figure 6:
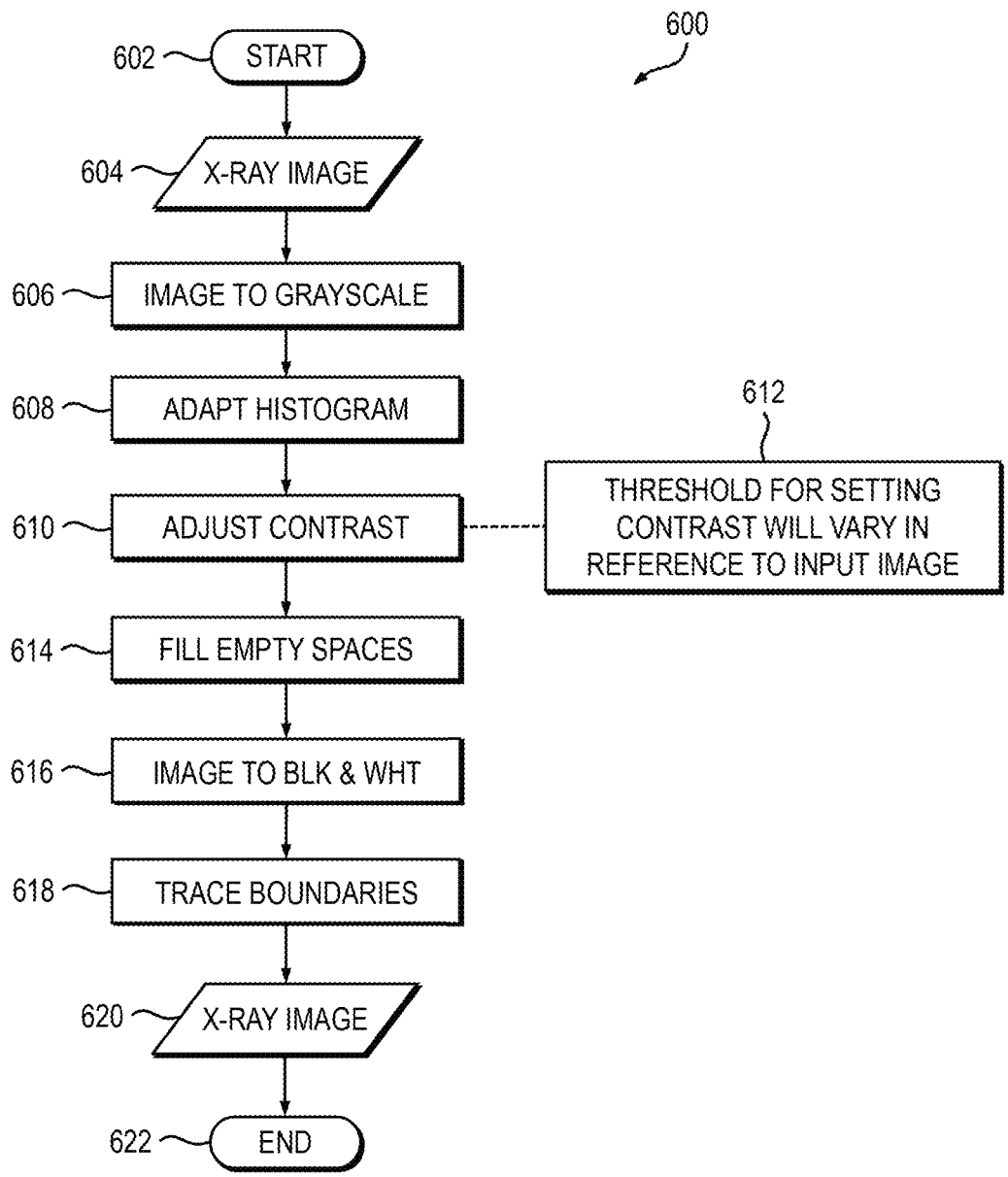
FIG. 6 is a flow diagram depicting at least a portion of an exemplary method for performing curvature deviation with edge detection for enhancing the accuracy of identifying the presence of a fracture in a digitized x-ray image, according to an embodiment of the invention.

FIG. 6 is a flow diagram depicting at least a portion of an exemplary method 600 for performing curvature deviation with edge detection, according to an embodiment of the invention. This method is preferably utilized in conjunction with the illustrative method 100 of FIG. 1 for enhancing the accuracy of identifying the presence of a fracture in a digitized x-ray image. The method 600 initially follows the same steps of image processing performed in the pixel intensity detection method 100 shown in FIG. 1, and then method 600 adds boundary tracing.

Specifically, the method 600 begins in step 602, which may include performing an initialization routine for setting certain registers, arrays, variables, etc., to known values (e.g., zero) for subsequent use in the method. In step 604, the method 600 receives, as an input, a digitized x-ray image to be analyzed for the presence of fractures. Prior to conducting boundary tracing and curvature deviation detection of the x-ray image, the method 600, like the illustrative method 100 of FIG. 1, preferably performs one or more image processing routines to enhance the image resolution or otherwise optimize the image to improve an accuracy of the fracture identification process.

As previously stated, since the digitized input x-ray image is generally an RGB image, step 606 converts the image to a grayscale image. A histogram of the grayscale image is then adapted in step 608, such as by performing histogram equalization. Histogram equalization, also referred to as histogram normalization, usually increases the global contrast of many images. Through this adjustment, image intensities can be more optimally distributed on the histogram, which allows for areas of lower local contrast to gain a higher contrast. Thus, in one or more embodiments, adapting the histogram of the grayscale image in step 608 preferably involves equalizing pixel intensities throughout the image.

In step 610, a contrast of the output image generated in step 608 is adjusted to a prescribed optimal range. Thresholds 612 for setting the image contrast are preferably supplied as input parameters for step 610 and will vary in reference to the particular input image. Although the present invention contemplates various ways to perform image contrast adjustment, one way to achieve this is by using the MATLAB® image processing toolbox command imadjust( ), as previously stated.

Figure 7:
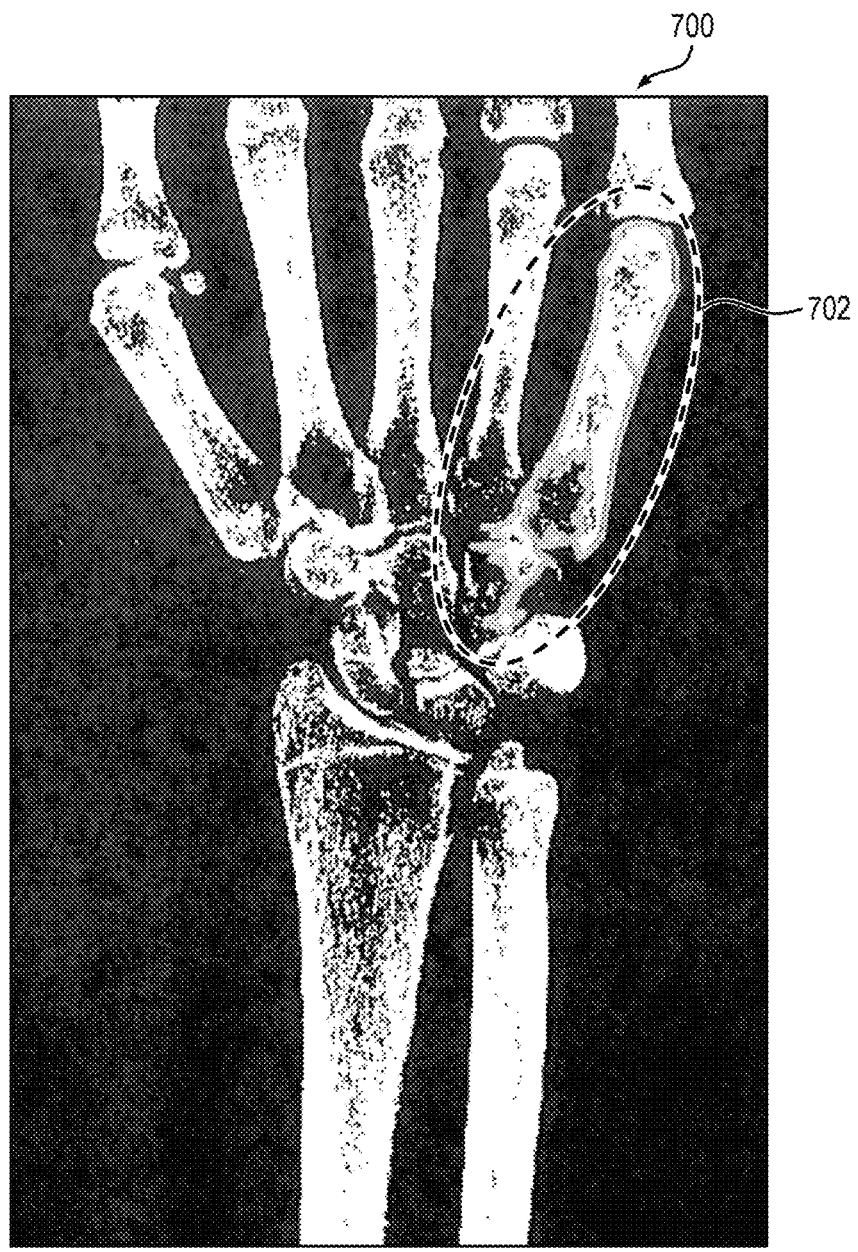
FIG. 7 conceptually depicts an exemplary modified x-ray image that may be generated as an output of the illustrative method shown in FIG. 6, according to an embodiment of the present invention.

With continued reference to FIG. 6, after performing the image preprocessing set forth in steps 606, 608 and 610, the method 600 fills in empty (interior) spaces of the image in step 614. The image is then converted from grayscale to a black and white image in step 616, and the boundaries of each white region are traced in step 618 to generate a modified x-ray image in step 620 that includes a boundary of interest defining a region to be evaluated for the presence of a fracture. The method 600 ends in step 622. FIG. 7 conceptually depicts an exemplary modified x-ray image 700 that may be generated as an output in step 620, according to an embodiment of the invention. As shown in FIG. 7, the modified image 700 includes a boundary of interest 702 which is used to detect the fracture using a curvature deviation detection method described in further detail herein below in connection with FIG. 8.

More particularly, FIG. 8 is a flow diagram depicting at least a portion of an exemplary method 800 for determining the curvature of a boundary of interest to enhance the accuracy of fracture detection in a digitized x-ray, according to an embodiment of the invention. The method 800 beings in step 802, which may include performing an initialization routine for setting certain registers, arrays, variables, etc., to known values (e.g., zero) for subsequent use in the method. In step 804, the method 800 receives, as an input, the modified x-ray image generated using the illustrative method 600 shown in FIG. 6, which includes a boundary of interest. After tracing the boundary of a region in the digitized x-ray image (step 618 of method 600 in FIG. 6), step 806 detects the boundary coordinates to extract an interest boundary enclosing a region to be evaluated for the presence of fractures. In one or more embodiments, the interest boundary is extracted in the form of a scatter plot, although embodiments of the invention are not limited to this data format. As is well known by those skilled in the art, a scatter plot is often used to show the relationship between two variables; typically, a symbol (e.g., a dot, bar, etc.) is used to represent a data pair.

Using the scatter plot data corresponding to the extracted interest boundary, step 808 preferably performs a quadratic curve fitting to this scatter plot. As will be known by those skilled in the art, a quadratic curve may be represented by the expression $y = ax^2 + bx + c$, where x and y are axis coordinates, and the numbers a, b, and c are coefficients of the expression and may be distinguished by calling them, respectively, the quadratic coefficient, the linear coefficient and the constant or free term. This quadratic curve is then converted to a parametric representation in step 810. The parametric representation is preferably of the form:

$$x = t + d; \text{ and}$$

$$y = e(t)^2 + f,$$

where d, e and f are coefficients, and t is the parameter, such that a point (x, y) is on the quadratic curve if and only if there is a value of t such that these two equations generate that point.

A curvature, $\kappa(t)$, of the quadratic curve is then calculated in step 812 from the parametric representation generated in step 810 (in units of meters $(m)^{-1}$). Optionally, the curvature of the quadratic curve is plotted in step 814, and the method 800 ends at step 816. Using the curvature plotted in step 814, a fracture is determined by detecting a change in curvature values of fractured bones compared to normal bones. By way of example only and without limitation, FIGS. 9A through 14 depict an illustrative process for detecting a fracture using curvature deviation detection as set forth in method 800, according to one or more embodiments of the invention. From these figures, a comparison can be made between how a normal bone behaves in the analysis and how different a fractured bone behaves, and how techniques in accordance with embodiments of the invention are used to beneficially detect a fracture from the digitized x-ray image with enhanced accuracy.

FIGS. 9A and 9B are an exemplary grayscale x-ray image 900 and a corresponding black and white x-ray image 910 after performing image preprocessing (e.g., histogram equalization, contrast adjustment, etc.), respectively, without any fractures (i.e., normal bones). For this example, the region of interest 912 represents a portion of a normal fifth metacarpal bone. Using method 800 (FIG. 8), from the image 910, an extracted boundary of interest is obtained. This extracted boundary can be expressed using a scatter plot, as previously stated.

Figure 10:
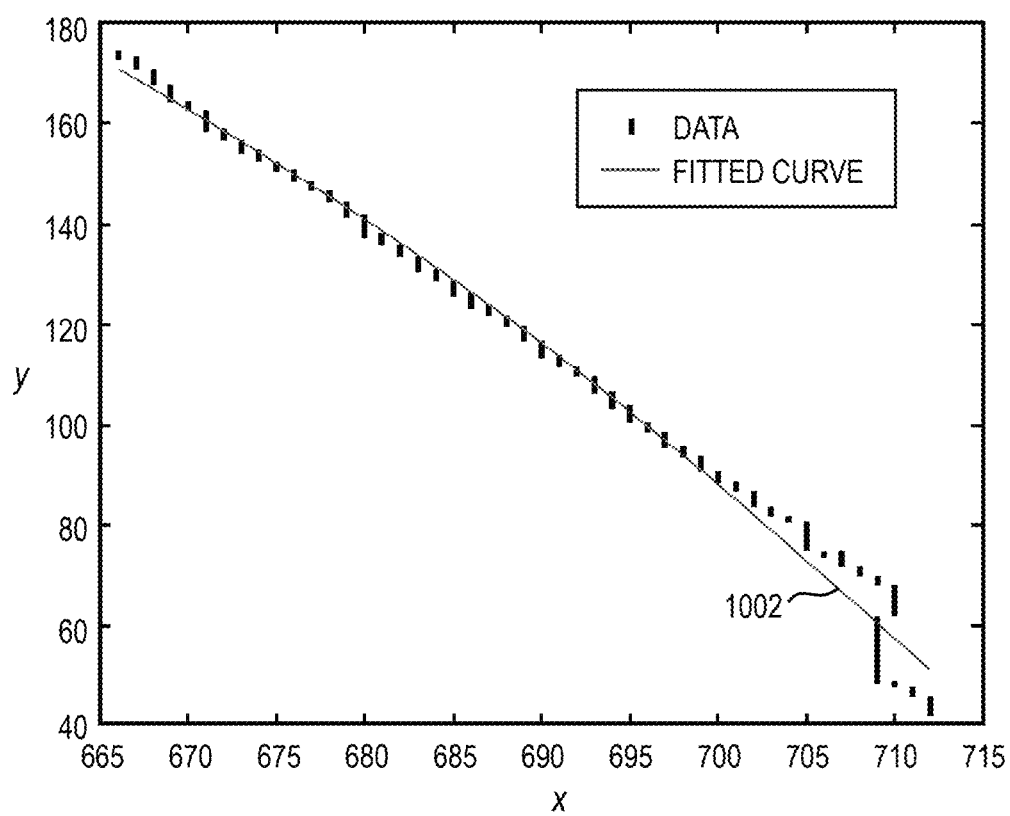
FIG. 10 is graph depicting an exemplary scatter plot representing an extracted boundary in a prescribed region of interest identified in FIG. 9B, along with a corresponding quadratic curve fitted to the extracted boundary, according to an embodiment of the present invention.
Figure 11:
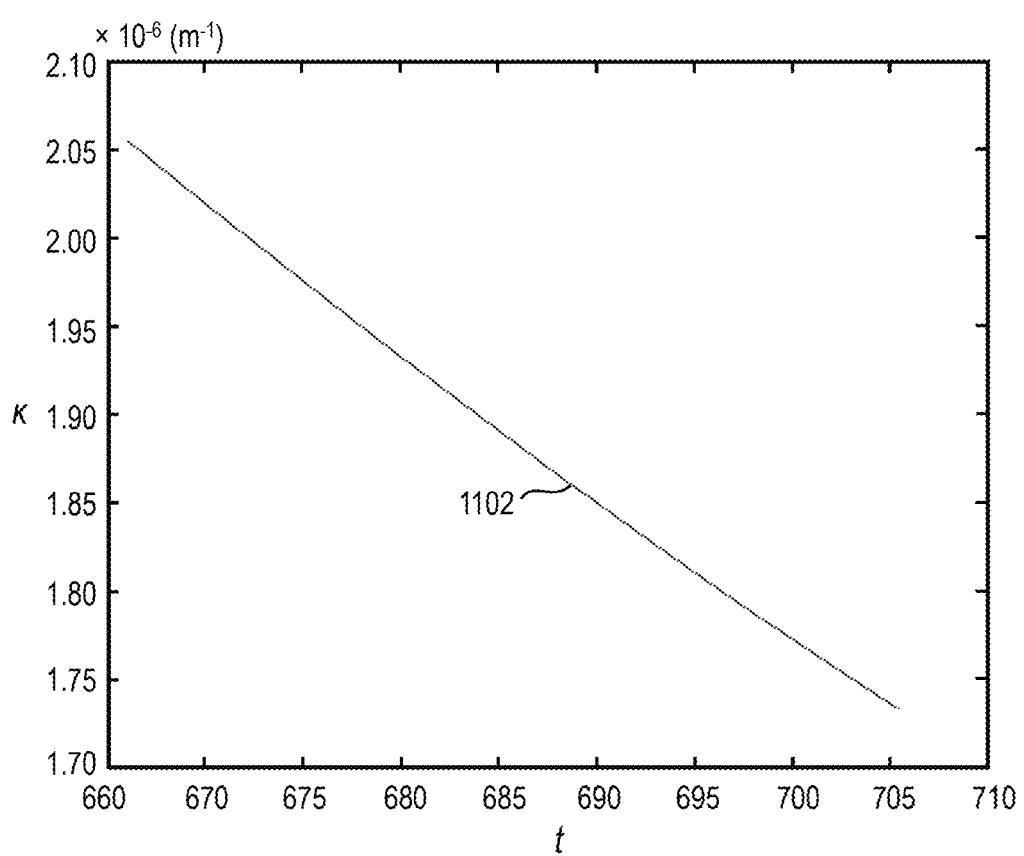
FIG. 11 is a graph depicting an exemplary plot of a curvature κ(t) of the illustrative quadratic curve shown in FIG. 10, according to an embodiment of the present invention.

FIG. 10 is graph depicting an exemplary scatter plot representing an extracted boundary in a prescribed region of interest 912 identified in FIG. 9B, along with a corresponding quadratic curve 1002 fitted to the extracted boundary, according to an embodiment of the invention. With reference to FIG. 10, the scatter plot comprises a plurality of data symbols. From this scatter plot data, the quadratic curve 1002 is fitted to the extracted boundary. A curvature $\kappa(t)$ of the quadratic curve 1002 fitted to the boundary is then determined. FIG. 11 is a graph depicting a plot 1102 of the curvature $\kappa(t)$ of the illustrative quadratic curve 1002 shown in FIG. 10, according to an embodiment of the invention. As apparent from FIG. 11, the curvature is relatively linear, decreasing from a value of about $2.05 \times 10^{-6}$ at about t=662, to a value of about $1.73 \times 10^{-6}$ at about t=705.

Figure 12A:
FIGS. 12A and 12B are an exemplary grayscale x-ray image and a corresponding black and white x-ray image after performing image preprocessing, respectively, the images having at least one fracture present.
Figure 12B:
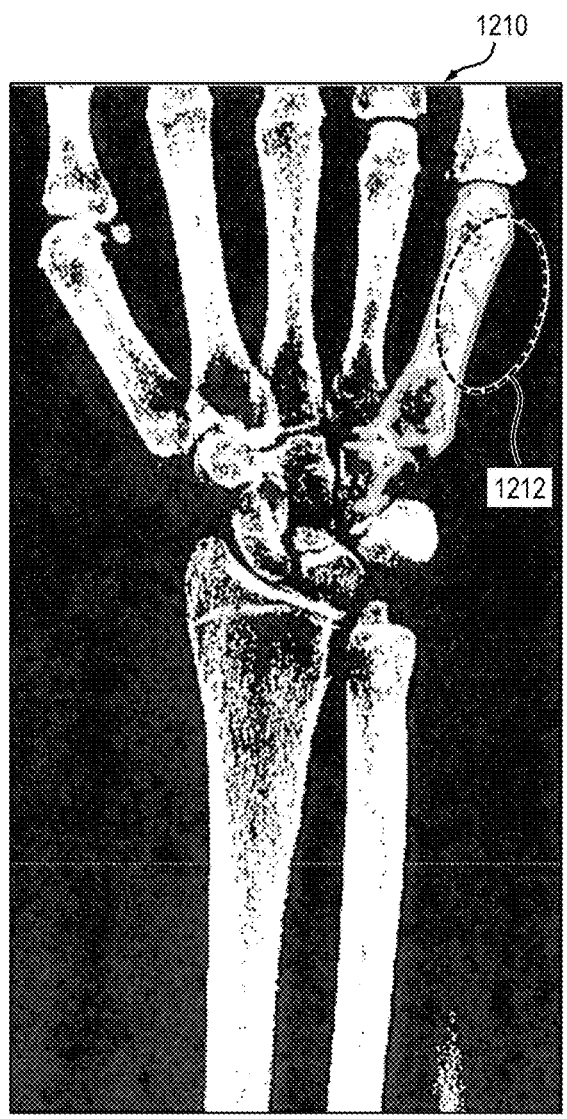

The curvature results shown in FIG. 11 obtained from a digitized x-ray image for a normal bone will now be compared with an image including a fracture in the fifth metacarpal bone. Specifically, FIGS. 12A and 12B are an exemplary grayscale x-ray image 1200 and a corresponding black and white x-ray image 1210 after performing image preprocessing (e.g., histogram equalization, contrast adjustment, etc.), respectively. The exemplary image 1210 shown in FIG. 12B includes an identified region of interest 1212 representing a portion of a normal fifth metacarpal bone that contains a fracture. Using the illustrative method 800 shown in FIG. 8, from the image 1210, an extracted boundary of interest is obtained. This extracted boundary can be expressed using a scatter plot.

Figure 13:
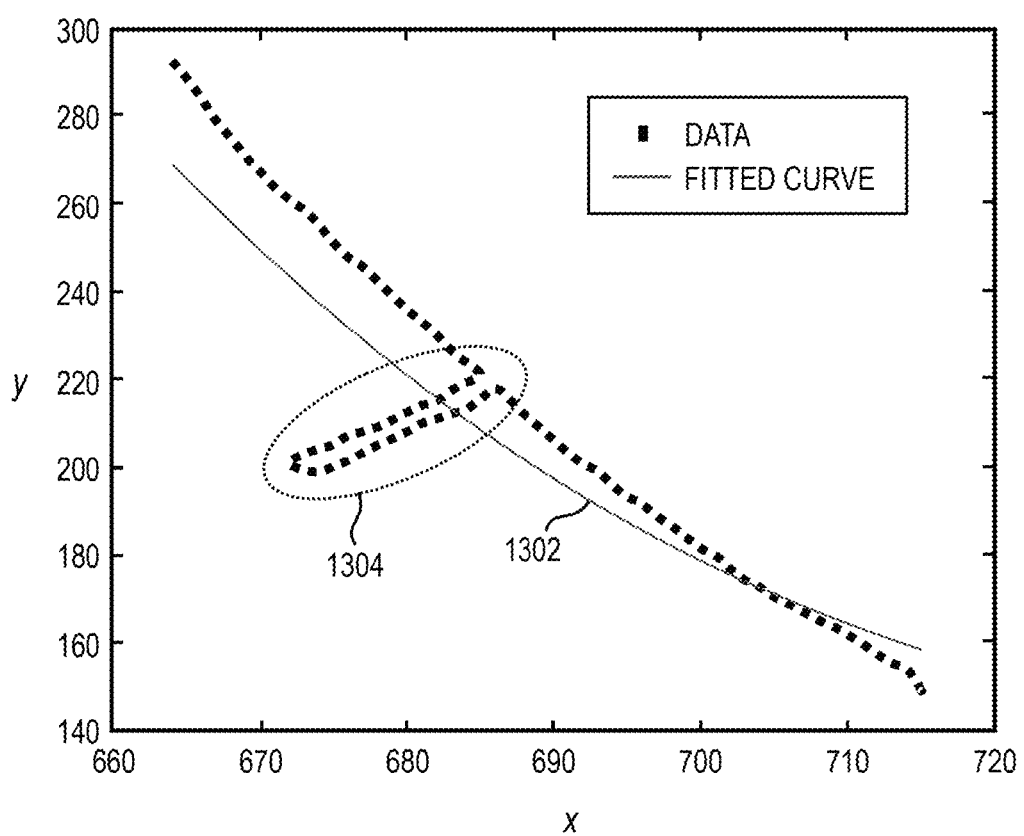
FIG. 13 is graph depicting an exemplary scatter plot representing an extracted boundary in a prescribed region of interest identified in FIG. 12B, along with a corresponding quadratic curve fitted to the extracted boundary, according to an embodiment of the invention.

FIG. 13 is graph depicting an exemplary scatter plot representing an extracted boundary in the prescribed region of interest 1212 identified in FIG. 12B, along with a corresponding quadratic curve 1302 fitted to the extracted boundary, according to an embodiment of the invention. With reference to FIG. 13, the scatter plot comprises a plurality of data symbols. In this exemplary case, the crack in the bone can be clearly seen, as indicated by region 1304 on the scatter plot. From this scatter plot data, the quadratic curve 1302 is fitted to the extracted boundary. However, unlike for the normal fifth metacarpal bone scenario, where the quadratic curve 1002 appears to closely follow the data points in the corresponding scatter plot in FIG. 10, the fitted quadratic curve 1302 representing a fifth metacarpal bone with a fracture exhibits a pronounced deviation from its corresponding scatter plot in FIG. 13. This deviation is attributable primarily to the presence of a disturbance, indicated by region 1304 in the extracted boundary resulting from the presence of a fracture.

Figure 14:
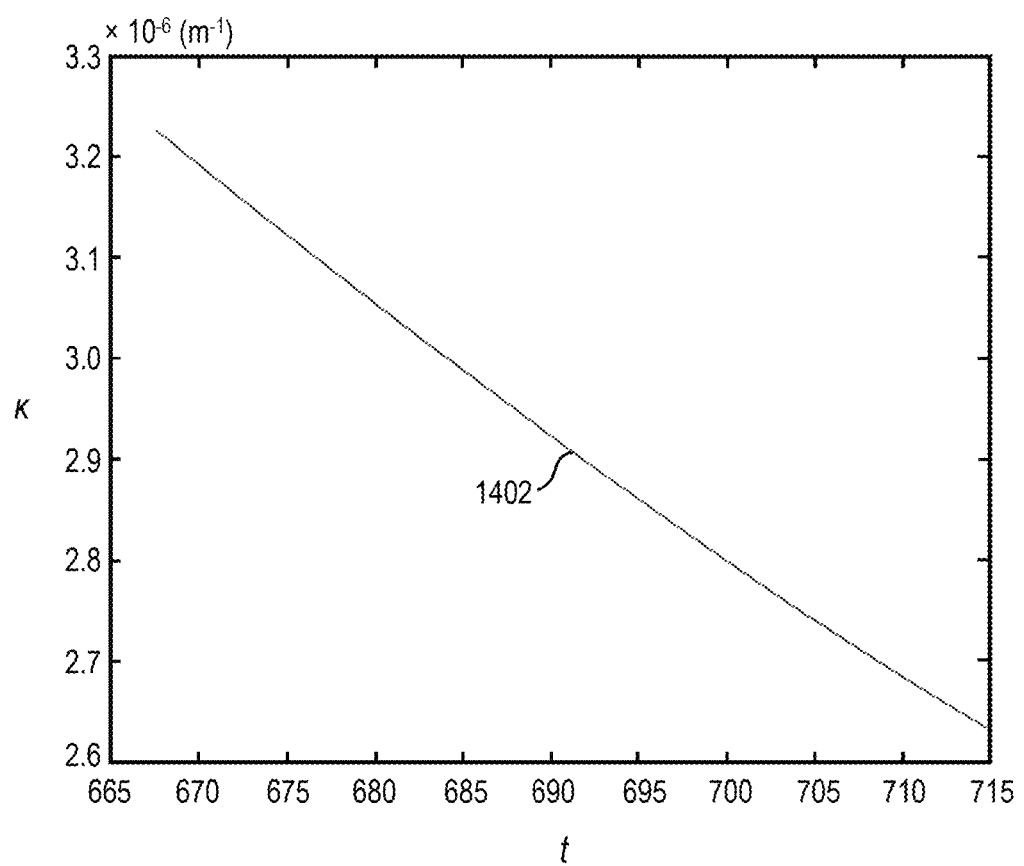
FIG. 14 is a graph depicting a plot of the curvature, κ(t), of the illustrative quadratic curve shown in FIG. 13, according to an embodiment of the present invention.

A curvature $\kappa(t)$ of the quadratic curve 1302 fitted to the extracted boundary (FIG. 13) is subsequently determined. FIG. 14 is a graph depicting a plot 1402 of the curvature $\kappa(t)$ of the illustrative quadratic curve 1302 shown in FIG. 13, according to an embodiment of the invention. As apparent from FIG. 14, the amount of curvature is considerably different compared to the curvature trend for the normal bone example shown in FIG. 11, decreasing from a value of about $3.24 \times 10^{-6}$ $m^{-1}$ at about t=668, to a value of about $2.64 \times 10^{-6}$ $m^{-1}$ at about t=715.

Figure 15:
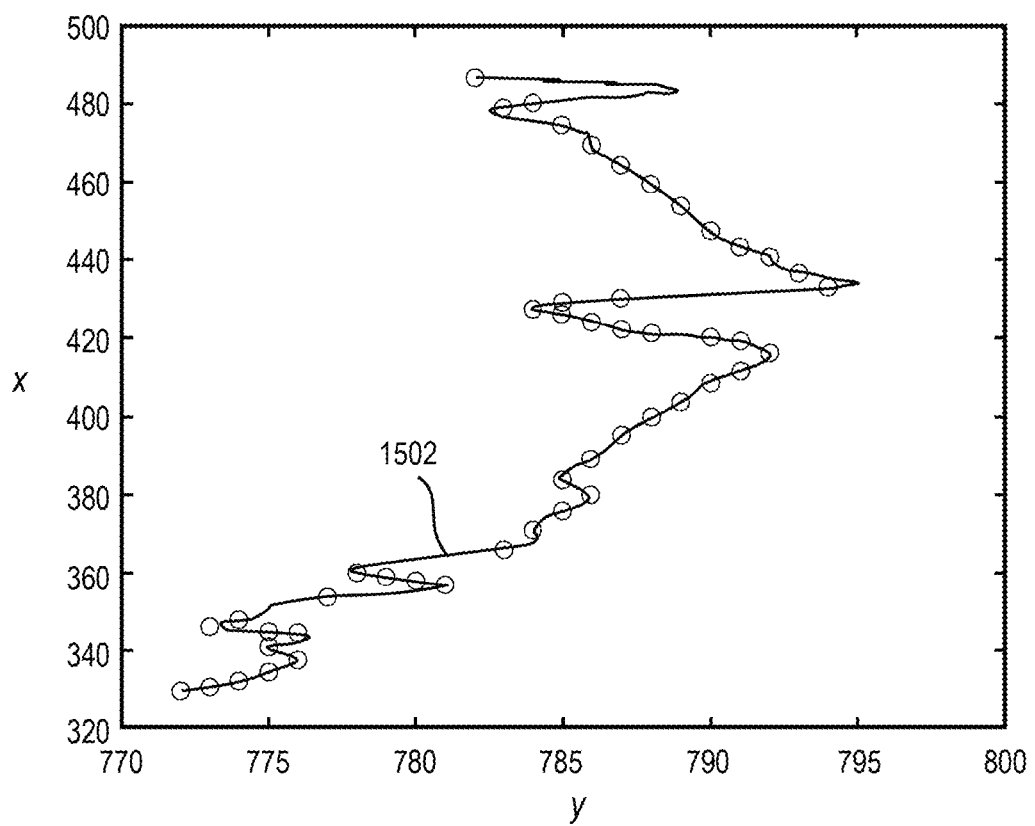
FIG. 15 is a graph depicting an exemplary spline fitting to the extracted boundary plotted in FIG. 13, according to an embodiment of the invention.

In one or more embodiments, a spline fitting technique is used to determine a rate of change of curvature throughout an extracted boundary. Specifically, a spline fitting to the extracted boundary is performed and a rate of change of curvature throughout the boundary is plotted. FIG. 15 is a graph depicting an exemplary spline fitting 1502 to the extracted boundary plotted in FIG. 13, according to an embodiment of the invention. As will be known by those skilled in the art, a spline fit is a data analysis methodology for estimating, via a least squares criterion, the parameters in a spline polynomial model. This technique is commonly used to fit curves that have different shapes in different areas of a horizontal axis variable. Knot points are defined to delineate these different regions. Separate spline polynomials are fit in these different regions. A distinction of spline fitting is that the fitted curve will be smooth at the knot points.

Figure 16:
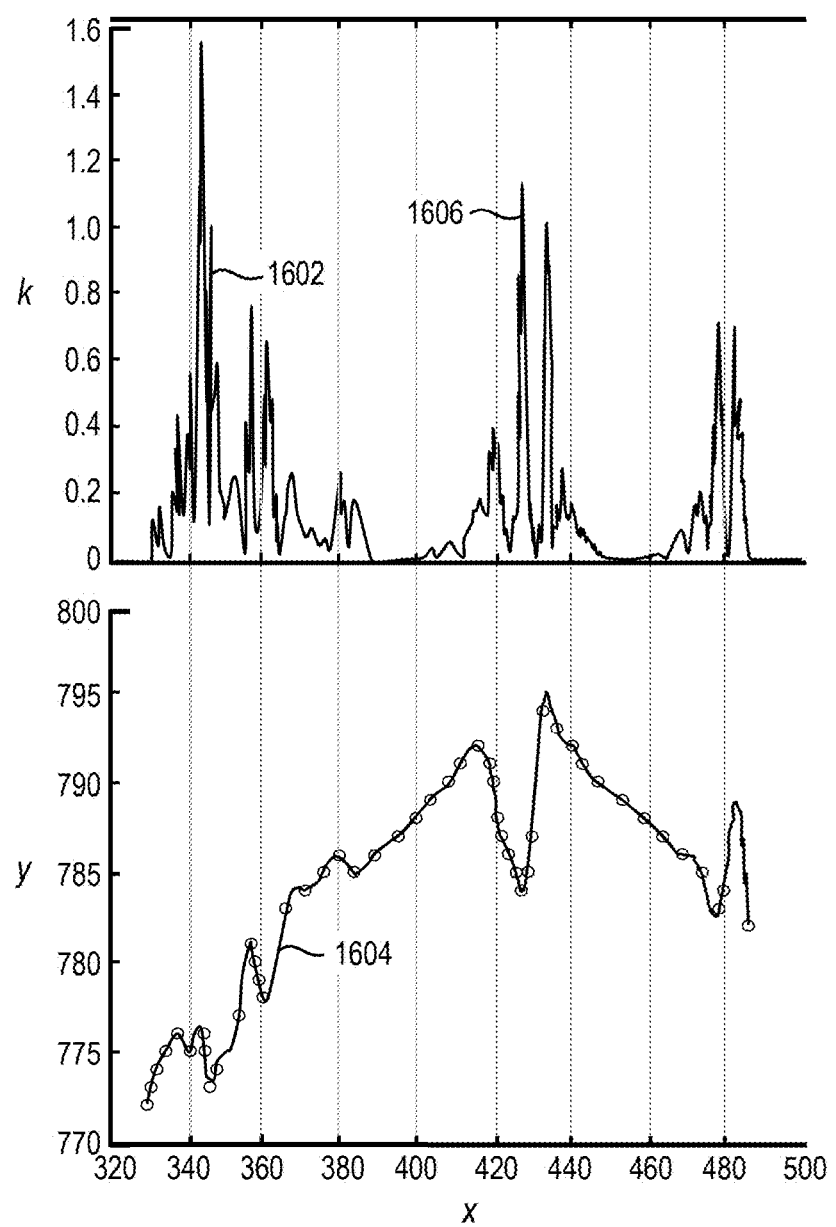
FIG. 16 is a graph depicting a B-spline plot and a rate of change of curvature plot corresponding to an extracted boundary of interest, according to an embodiment of the present invention.

The extracted boundary is fitted with a basis spline, or B-spline, and a rate of change of curvature $\kappa(t)$ is plotted, as represented by the illustrative plot 1602 shown in FIG. 16. In the context of numerical analysis, a B-spline is a spline function that has minimal support with respect to a given degree, smoothness, and domain partition. In FIG. 16, the exemplary spline fitting shown in FIG. 15 is rotated by 90 degrees as plot 1604, so that its x-axis aligns with the x-axis of the rate of change of curvature $\kappa(t)$ plot 1602 for comparison purposes. As evident from plot 1602, there is a spike 1606 in the rate of change of curvature $\kappa(t)$; the spike 1606, along with its two adjacent peaks, indicates the presence of a fracture.

In one or more embodiments of the invention, machine learning can be used as another technique for detecting the presence of a hairline fracture in a digitized x-ray image, either alone in combination with at least one of the other methods for fracture detection according to aspects of the invention previously described herein. Each of the different algorithms for detecting a fracture in a digitized x-ray image may have different success rates depending on the particular conditions (e.g., location of the fracture, type of bone, type of fracture, etc.). Consequently, more than fracture detection algorithm may be employed.

When using multiple algorithms for detecting a fracture in a digitized x-ray image, a confidence factor is preferably assigned to each algorithm, according to embodiments of the invention. The confidence factor, in some embodiments, may be in the form of a statistical likelihood (i.e., a probability) that the algorithm correctly identifies the presence of a fracture, without generating an indication when no facture is present (a false positive) and/or without missing a fracture that is actually present (a false negative).

Figure 17:
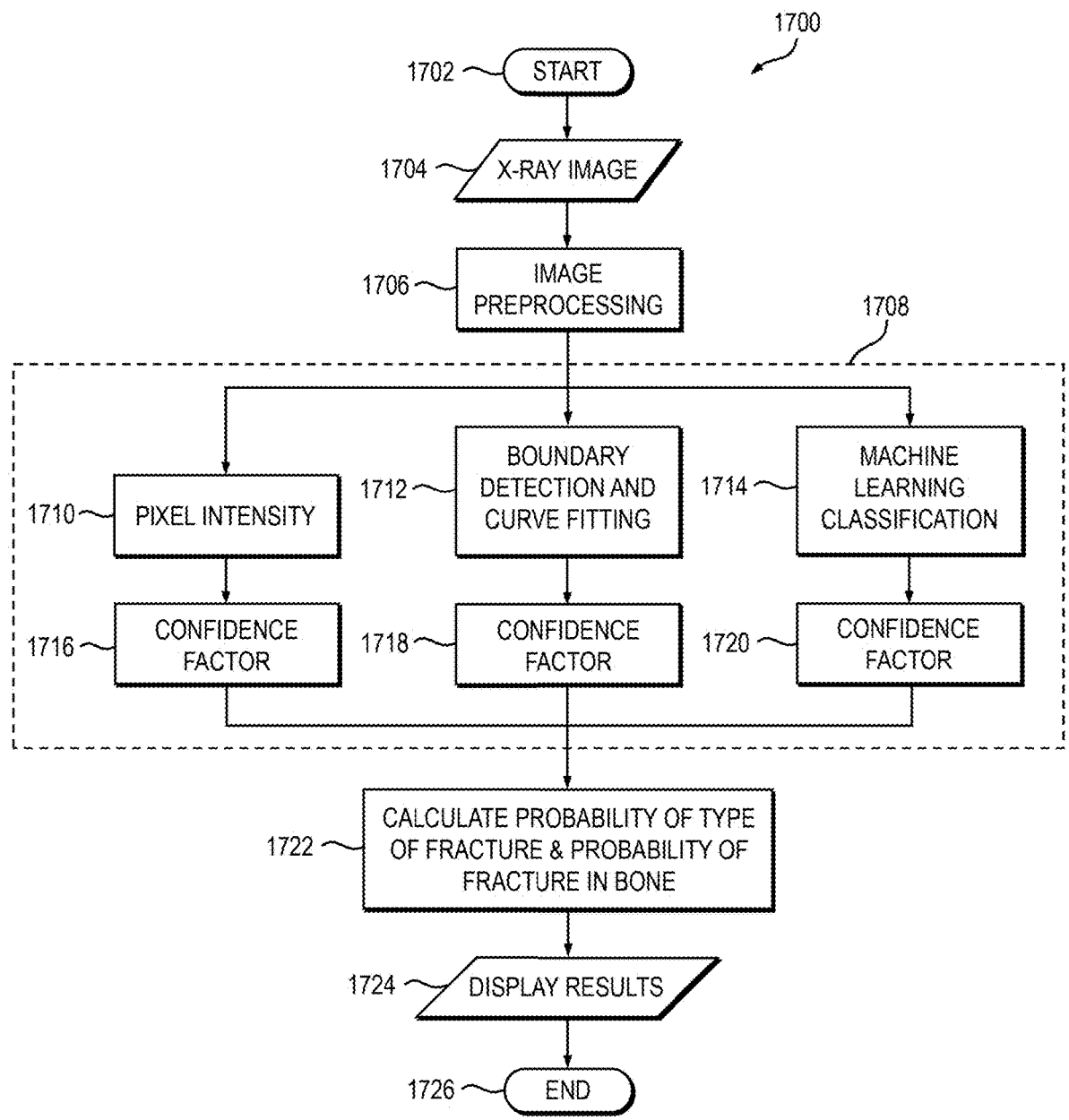
FIG. 17 is a flow diagram depicting at least a portion of an exemplary method for identifying a fracture in a digitized x-ray image which utilizes multiple detection algorithms in combination with a confidence factor for generating a final output result, according to an embodiment of the present invention.

FIG. 17 is a flow diagram depicting at least a portion of an exemplary method 1700 which utilizes multiple fracture detection algorithms in combination with a confidence factor for generating a final output result, according to an embodiment of the invention. The method 1700 begins in step 1702, which may include an initialization procedure for setting certain registers, arrays, variables, etc., to known values (e.g., zero) for use in a subsequent step of the method. Next, in step 1704, the method 1700 receives, as an input, a digitized x-ray image to be analyzed for the presence of fractures. In step 1706, one or more image preprocessing routines (e.g., histogram equalization, contrast adjustment, etc.) are optionally performed for optimizing the image resolution and/or quality to beneficially enhance an accuracy of the fracture identification.

The preprocessed image generated in step 1706 is then used for preferably performing multiple fracture detection algorithms, each of which has been described herein above, identified collectively as 1708. Although only three fracture detection methodologies are shown, it is to be appreciated that embodiments of the invention not limited to the fracture detection methodologies shown. In this illustrative embodiment, fracture detection algorithms 1708 may include a pixel intensity algorithm 1710 (e.g., at least a portion of the method 100 shown in FIG. 1), a boundary detection and curve fitting algorithm 1712 (e.g., at least a portion of the method 800 shown in FIG. 8), and a machine learning classification algorithm 1714. A machine learning classification algorithm 1714 suitable for use in connection with embodiments of the invention employs a region-based convolution neural network framework on the X-ray database. This machine learning computer vision algorithm classifies and localizes bones with a detected fracture/hairline fracture. The use of other fracture detection algorithms is similarly contemplated.

Each of these fracture detection algorithms 1708 preferably has a confidence factor associated therewith. For example, the pixel intensity algorithm 1710 has a first confidence factor 1716 associated therewith, the boundary detection and curve fitting algorithm 1712 has a second confidence factor 1718 associated therewith, and the machine learning classification algorithm 1714 has a third confidence factor 1720 associated therewith. As previously stated, the confidence factor assigned to each fracture detection methodology may, in some embodiments, be in the form of a probability that the particular algorithm accurately identifies the presence of a fracture in the digitized x-ray image.

The output generated by each of the fracture detection methodologies 1710, 1712, 1714, along with their respective assigned confidence factors 1716, 1718, 1720, are supplied as inputs to a probability calculation module in step 1722. The probability calculation module (1722) is preferably configured to determine the probability of the presence of a fracture in a bone and a probability of a type of fracture.

The determination of fracture diagnosis may be based on multiple methodologies, according to one or more embodiments of the invention. Multiple redundant methodologies that can determine the existence of a hairline fracture/crack in an X-ray image have been previously described, including, for example, image processing using pixel intensity, boundary detection, curvature analysis, machine learning, etc. Each of these algorithms will produce an output result having a certain probability, P, of the X-ray image having a correctly detected hairline fracture associated therewith. Weights, $w_i$, can be assigned for each methodology, with each weight representing a confidence of that particular methodology generating a correct result. A sum of these weights will add up to one as follows:

$$w_{ip}+w_{ca}+w_{ml}+\ldots+w_n=1.0,$$

where $w_{ip}$ is a weight given to an image processing methodology, $w_{ca}$ is a weight assigned to a curvature analysis methodology, $w_{ml}$ is weight assigned to a machine learning methodology, and $w_n$ is a weight given to other fracture detection methodologies.

Confidence factors of the respective results from the particular fracture detection methodologies are preferably determined as probability results multiplied by their corresponding weights. A final probability, $P_{final}$, will be determined as a sum of these confidence factors as follows:

$$P_{final}=w_{ip} \cdot P_{ip}+w_{ca} \cdot P_{ca}+w_{ml} \cdot P_{ml}+\ldots+w_n \cdot P_n,$$

where $P_{ip}$ is a probability of yielding a correct result using image processing, Pea is a probability of yielding a correct result using curvature analysis, $P_{ml}$ is a probability of yielding a correct result using machine learning, and $P_n$ is a probability of yielding a correct result using another fracture detection methodology.

As an illustration, with reference to FIG. 17, the confidence factor 1716 using the pixel intensity algorithm 1710 renders a probability $P_{ip}$, the confidence factor 1718 using the boundary detection and curve fitting algorithm 1712 renders a probability $P_{ca}$, and the confidence factor 1720 using the machine learning classification algorithm 1714 renders a probability $P_{ml}$. The final probability determined by the probability calculation module in step 1722 will be the weighted sum of these confidence factors as:

$$P_{final}=w_{ip} \cdot P_{ip}+w_{ca} \cdot P_{ca}+w_{ml} \cdot P_{ml},$$

where the weights sum up to 1.0 and can be assigned different values based on the importance of each category of 1710, 1712 and 1714, among other factors.

In step 1724, prescribed output results of the method 1700 are presented, to an attending physician, radiologist or other user, to facilitate the diagnostic process. The results presented are preferably in the form of a visual indication (e.g., symbol, region highlighting, etc.) placed on the digitized x-ray image proximate to the location of a predicted fracture. In this regard, the output results may be in the form of coordinates which identify the location of a predicted fracture on the x-ray image. The results may also include the probability of the presence of a fracture and probability of a certain type of fracture. The method 1700 then ends at step 1726.

Embodiments of the invention may be implemented together with virtually any type of computer, regardless of the platform being suitable for storing and/or executing program code. By way of example only and without limitation, FIG. 18 is a block diagram depicting at least a portion of an illustrative computing system 1800 suitable for executing program code related to the proposed method(s).

The computing system 1800 is only one example of a suitable computer system and is not intended to suggest any limitation as to the scope of use or functionality of embodiments of the invention described herein, regardless, whether the computer system 1800 is capable of being implemented and/or performing any of the functionality set forth hereinabove. In the computer system 1800, there are components, which are adapted for connection to and operational with numerous other general-purpose or special-purpose computing system environments or configurations. Examples of well-known computing systems, environments, and/or configurations that may be suitable for use with computer system 1800 include, but are not limited to, personal computer systems, server computer systems (i.e., servers), thin clients, thick clients, hand-held or laptop devices, mobile devices, multiprocessor systems, microprocessor-based systems, programmable consumer electronics, network PCs, minicomputer systems, mainframe computer systems, and distributed cloud computing environments that include any of the above systems or devices, and the like.

The computer system 1800 may be described in the general context of computer system-executable instructions, such as program modules, being executed by the computer system 1800. Generally, program modules may include routines, programs, objects, components, logic, data structures, and so on that perform particular tasks or implement particular abstract data types. The computer system 1800 may be practiced in distributed cloud computing environments where tasks are performed by remote processing devices that are linked through a communications network. In a distributed cloud computing environment, program modules may be located in both local and remote computer system storage media, including memory storage devices.

Figure 18:
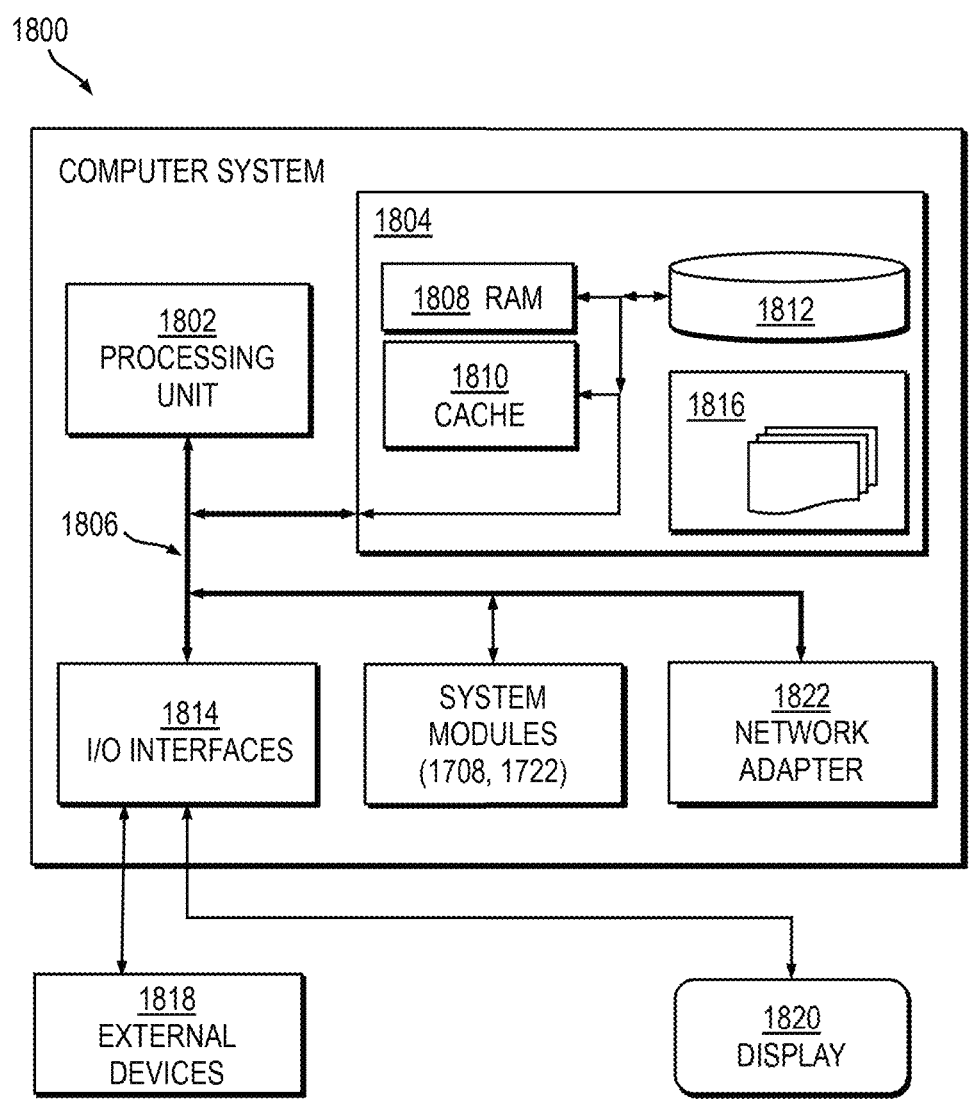
FIG. 18 is a block diagram depicting at least a portion of an illustrative computing system suitable for executing program code related to the proposed methods, according to an embodiment of the present invention.

As shown in FIG. 18, the computer system 1800 is shown in the form of a general-purpose computing device. Components of computer system 1800 may include, but are not limited to, one or more processors or processing units 1802, a system memory 1804, and a bus 1806 that couples various system components including system memory 1804 to the processor 1802. Bus 1806 represents one or more of any of several types of bus structures, including a memory bus or memory controller, a peripheral bus, an accelerated graphics port, and a processor or local bus using any of a variety of bus architectures. By way of example, and without limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 1800 typically includes a variety of computer system readable media. Such media may be any available media that is accessible by computer system 1800, and it includes both, volatile and non-volatile media, removable and non-removable media.

The system memory 1804 may include computer system readable media in the form of volatile memory, such as random-access memory (RAM) 1808 and/or cache memory 1810. Computer system 1800 may further include other removable/non-removable, volatile/non-volatile computer system storage media. By way of example only, a storage system 1812 may be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media may be provided. In such instances, each can be connected to bus 1806 by one or more data media interfaces. As will be further depicted and described below, memory 1804 may include at least one program product having a set (e.g., at least one) of program modules that are configured to carry out the functions of embodiments of the invention.

The program/utility, having a set (at least one) of program modules 1816, may be stored in memory 1804 by way of example, and not limiting, as well as an operating system, one or more application programs, other program modules, and program data. Each of the operating systems, one or more application programs, other program modules, and program data or some combination thereof, may include an implementation of a networking environment. The program modules 1816 generally carry out the functions and/or methodologies of embodiments of the invention, as described herein.

The computer system 1800 may also communicate with one or more external devices 1818 such as a keyboard, a pointing device, a display 1820, etc.; one or more devices that enable a user to interact with the computer system 1800; and/or any devices (e.g., network card, modem, etc.) that enable the computer system 1800 to communicate with one or more other computing devices. Such communication can occur via input/output (I/O) interfaces 1814. Still yet, the computer system 1800 may communicate with one or more networks such as a local area network (LAN), a general wide area network (WAN), and/or a public network (e.g., the Internet) via a network adapter 1822. As depicted, the network adapter 1822 may communicate with the other components of the computer system 1800 via the bus 1806. Although not explicitly shown, other hardware and/or software components could be used in conjunction with the computer system 1800. Examples, include, but are not limited to: microcode, device drivers, redundant processing units, external disk drive arrays, redundant array of independent disks (RAID) systems, tape drives, and data archival storage systems, etc.

Additionally, further components of the system for identifying a fracture in a digitized x-ray image may be connected to the bus 1806. This may include, for example, one or more image preprocessing modules configured to perform image preprocessing (106, 108, 110 in FIG. 1), a line tracing module configured to perform image line tracing (114 in FIG. 1), pixel intensity calculation and threshold detection modules (e.g., 116, and 118 in FIG. 1), boundary tracing module (e.g., 618 in FIG. 6), a boundary coordinate detection module configured to detect boundary coordinates (e.g., 806 in FIG. 8), a quadratic curve fitting module configured to perform quadratic curve fitting (e.g., 808 in FIG. 8), a curvature calculation module configured to determine a curvature of the quadratic curve (e.g., 812 in FIG. 8) and a probability calculation module configured to determine a probability of the presence and/or type of fracture (1722 in FIG. 17).

The present invention may be a system, a method, and/or a computer program product at any possible technical level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not intended to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire or the air.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission routers, firewalls, switches, gateway computers and/or edge servers. A network adapter card or network interface in each computer/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer, for example, through the Internet using an Internet Service Provider (ISP). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize and configure the electronic circuitry, in order to perform aspects of the present invention.

Aspects of the present invention are described herein with reference to flowchart instructions and/or block diagrams of methods, apparatus (systems), and computer program products according to embodiments of the invention. It will be understood that each block of the flowchart instructions and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram blocks or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be appreciated that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The illustrations of embodiments described herein are intended to provide a general understanding of the various embodiments, and they are not intended to serve as a complete description of all the elements and/or features of apparatus, methods and systems that might make use of the techniques described herein. Many other embodiments will become apparent to those skilled in the art given the teachings herein; other embodiments are utilized and derived therefrom, such that structural and logical substitutions and changes can be made without departing from the scope of this disclosure. It should also be noted that, in some alternative implementations, some of the steps of exemplary methods described herein may occur out of the order described or noted in the figures (where shown). The drawings are also merely representational and are not drawn to scale. Accordingly, the specification and drawings are to be regarded in an illustrative rather than a restrictive sense.

Reference made throughout this specification to "one embodiment" or "an embodiment" is intended to mean that a particular feature, structure, or characteristic described in connection with the embodiment is included in at least one embodiment of the claimed subject matter. It is to be understood that appearances of the phrase "in one embodiment" or "an embodiment" are not necessarily all referring to the same embodiment. Furthermore, embodiments may be referred to herein, individually and/or collectively, by the term "embodiment" merely for convenience and without intending to limit the scope of this application to any single embodiment or inventive concept if more than one is, in fact, shown. Thus, although specific embodiments have been illustrated and described herein, it is to be appreciated that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "above" and "below," where used, are intended to indicate positioning of elements or structures relative to each other as opposed to absolute elevation.

The corresponding structures, materials, acts, and equivalents of any means or step-plus-function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit thereof. The embodiments were chosen and described in order to best explain principles and practical applications, and to enable others of ordinary skill in the art to understand the various embodiments with various modifications as are suited to the particular use contemplated.

The abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the appended claims reflect, the claimed subject matter may lie in less than all features of a single embodiment. Thus, the following claims are hereby incorporated into the Detailed Description, with each claim standing on its own as separately claimed subject matter.

Given the teachings provided herein, one of ordinary skill in the art will be able to contemplate other implementations and applications of the techniques and disclosed embodiments according to aspects of the invention. Although illustrative embodiments have been described herein with reference to the accompanying drawings, it is to be understood that illustrative embodiments are not limited to those precise embodiments, and that various other changes and modifications may be made therein by one skilled in the art without departing from the scope or spirit of the appended claims.

What is claimed is:

1. A method for identifying one or more fractures in a digitized x-ray image, the method comprising:
    obtaining a digitized x-ray image;
    performing preprocessing on the digitized x-ray image to generate a modified x-ray image having enhanced resolution;
    partitioning the modified x-ray image into a two-dimensional array comprising a plurality of pixels;
    obtaining an intensity of each of the plurality of pixels in the modified x-ray image;
    evaluating each of the plurality of pixels in the modified x-ray image to determine whether at least a given one of the plurality of pixels has an intensity indicative of a black pixel;
    for each given pixel having an intensity indicative of a black pixel, flagging the given pixel when pixels immediately adjacent to and within a prescribed range of the given pixel have an intensity greater than a prescribed threshold value; and
    placing a visual indication of a possible fracture on the modified x-ray image corresponding to a location of each flagged pixel.

2. The method according to claim 1, wherein performing preprocessing on the digitized x-ray image comprises:
    adapting a histogram of the digitized x-ray image to equalize pixel intensities throughout the image; and
    adjusting a contrast of the digitized x-ray image as a function of at least one threshold parameter to generate the modified x-ray image.

3. The method according to claim 2, wherein adjusting the contrast of the digitized x-ray image comprising executing a MATLAB® image processing toolbox command imadjust ( ).

4. The method according to claim 1, wherein evaluating each of the plurality of pixels in the modified x-ray image is performed using line tracing, whereby the plurality of pixels are scanned along lines horizontally and vertically throughout the image.

5. The method according to claim 1, wherein evaluating each of the plurality of pixels in the modified x-ray image is performed as a function of at least one prescribed threshold value.

6. The method according to claim 1, wherein partitioning the modified x-ray image comprises controlling a resolution of the modified x-ray image by adjusting a pixel size of the plurality of pixels in the two-dimensional array.

7. The method according to claim 1, further comprising performing boundary detection and curvature deviation analysis to enhance an accuracy of identifying one or more fractures in the digitized x-ray image.

8. The method according to claim 7, wherein performing boundary detection comprises:
    filling in empty spaces of the modified x-ray image to generate an intermediate grayscale image;
    converting the intermediate grayscale image to a black and white image; and
    tracing a boundary of each white region in the black and white image to generate an output image that includes a boundary of interest defining a region to be evaluated for a presence of a fracture.

9. The method according to claim 8, wherein performing curvature analysis comprises:
    detecting boundary coordinates to extract an interest boundary enclosing the region to be evaluated for the presence of a fracture;
    generating a scatter plot corresponding to the extracted boundary of interest;
    performing a quadratic curve fitting to the scatter plot to generate a quadratic curve represented by an expression $y=ax^2+bx+c$, where x and y are axis coordinates, and a, b and c are quadratic coefficients;
    converting the quadratic curve to a parametric representation;
    calculating a curvature of the quadratic curve from the parametric representation; and
    determining whether there is a deviation in curvature in the region to be evaluated relative to a curvature of normal bones, the deviation in curvature being indicative of a presence of a fracture in the digitized x-ray image.

10. The method according to claim 9, wherein performing curvature analysis further comprises plotting a curvature of the quadratic curve, and wherein determining whether there is a deviation in curvature in the region to be evaluated relative comprises comparing the plot of curvature of the quadratic curve to a plot of curvature of a normal bone corresponding to the region to be evaluated.

11. The method according to claim 9, wherein calculating the curvature of the quadratic curve comprises performing spline fitting to determine a rate of change of curvature throughout the extracted boundary of interest.

12. The method according to claim 1, further comprising:
performing a plurality of fracture detection algorithms; and
assigning a confidence factor to each of the plurality of fracture detection algorithms, the confidence being indicative of a statistical likelihood that a corresponding one of the fracture detection algorithms correctly identifies the presence of a fracture in the digitized x-ray image.

13. The method according to claim 12, wherein the plurality of fracture detection algorithms comprises image processing, boundary detection, curvature analysis, and machine learning.

14. The method according to claim 12, further comprising determining a probability of the presence of a fracture in the digitized x-ray image and a probability of a type of fracture present, based at least in part on the confidence factors assigned to the plurality of fracture detection algorithms.

15. An apparatus for identifying one or more fractures in a digitized x-ray image, the apparatus comprising:
memory; and
at least one processor coupled with the memory, the at least one processor being configured: to obtain a digitized x-ray image; to perform preprocessing on the digitized x-ray image to generate a modified x-ray image having enhanced resolution; to partition the modified x-ray image into a two-dimensional array comprising a plurality of pixels; to obtain an intensity of each of the plurality of pixels in the modified x-ray image; to evaluate each of the plurality of pixels in the modified x-ray image to determine whether at least a given one of the plurality of pixels has an intensity indicative of a black pixel; for each given pixel having an intensity indicative of a black pixel, to flag the given pixel when pixels immediately adjacent to and within a prescribed range of the given pixel have an intensity greater than a prescribed threshold value; and to place a visual indication of a possible fracture on the modified x-ray image corresponding to a location of each flagged pixel.

16. The apparatus according to claim 15, wherein the at least one processor is further configured to perform preprocessing on the digitized x-ray image by adapting a histogram of the digitized x-ray image to equalize pixel intensities throughout the image, and adjusting a contrast of the digitized x-ray image as a function of at least one threshold parameter to generate the modified x-ray image.

17. The apparatus according to claim 15, wherein the at least one processor is further configured to evaluate each of the plurality of pixels in the modified x-ray image using line tracing, whereby the plurality of pixels are scanned along lines horizontally and vertically throughout the image.

18. The apparatus according to claim 15, wherein the at least one processor is further configured to evaluate each of the plurality of pixels in the modified x-ray image as a function of at least one prescribed threshold value.

19. The apparatus according to claim 15, wherein the at least one processor is further configured to perform boundary detection and curvature deviation analysis to enhance an accuracy of identifying one or more fractures in the digitized x-ray image.

20. The apparatus according to claim 19, wherein in performing boundary detection and curvature deviation analysis, the at least one processor is further configured: to fill in empty spaces of the modified x-ray image to generate an intermediate grayscale image; to convert the intermediate grayscale image to a black and white image; and to trace a boundary of each white region in the black and white image to generate an output image that includes a boundary of interest defining a region to be evaluated for a presence of a fracture.

* * * * *